US011311385B2

(12) United States Patent
Collazo et al.

(10) Patent No.: US 11,311,385 B2
(45) Date of Patent: Apr. 26, 2022

(54) SYSTEMS AND METHODS FOR CONVERTING A JOINT PROSTHESIS FROM A FIRST TYPE TO A SECOND TYPE IN-SITU

(71) Applicant: Howmedica Osteonics Corp., Mahwah, NJ (US)

(72) Inventors: Carlos E. Collazo, Old Greenwich, CT (US); Damon J. Servidio, Towaco, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 120 days.

(21) Appl. No.: 16/924,598

(22) Filed: Jul. 9, 2020

(65) Prior Publication Data

US 2021/0007855 A1     Jan. 14, 2021

Related U.S. Application Data

(60) Provisional application No. 62/873,514, filed on Jul. 12, 2019.

(51) Int. Cl.
*A61F 2/38*     (2006.01)
*A61F 2/30*     (2006.01)

(52) U.S. Cl.
CPC .............. *A61F 2/384* (2013.01); *A61F 2/389* (2013.01); *A61F 2/3859* (2013.01); *A61F 2002/30616* (2013.01); *A61F 2002/30621* (2013.01); *A61F 2002/3863* (2013.01)

(58) Field of Classification Search
CPC ......... A61F 2/384; A61F 2/389; A61F 2/3859
See application file for complete search history.

(56) References Cited

U.S. PATENT DOCUMENTS

| 4,888,021 A | 12/1989 | Forte et al. |
| 6,143,034 A | 11/2000 | Burrows |
| 8,628,579 B2 | 1/2014 | Ries et al. |

(Continued)

FOREIGN PATENT DOCUMENTS

WO     03059203 A1     7/2003

OTHER PUBLICATIONS

Extended European Search Report for Application No. 20185043 dated Nov. 30, 2020, 2 pages.

*Primary Examiner* — Jason-Dennis N Stewart
(74) *Attorney, Agent, or Firm* — Lerner, David, Littenberg, Krumholz & Mentlik, LLP

(57) ABSTRACT

A joint prosthesis system includes a femoral component that has an articular side, a bone facing side, and medial and lateral condylar portions. The medial and lateral condylar portions at least partially define an intercondylar recess located therebetween and have a first concave surface extending in a mediolateral direction across the medial and lateral condylar portions. A first modular component has a second concave surface and is connectable to the femoral component such that, when the first modular component is connected to the femoral component, the first and second concave surfaces come together to form a transverse opening extending in the mediolateral direction. A first tibial assembly has a baseplate component and a head extending therefrom. The head defines an axle opening that extends therethrough. An axle is configured to be received within the transverse opening and axle opening so as to connect the tibial assembly to the femoral component.

19 Claims, 16 Drawing Sheets

(56) References Cited

U.S. PATENT DOCUMENTS

| | | |
|---|---|---|
| 9,649,205 B2 | 5/2017 | Dees, Jr. |
| 10,010,422 B2 | 7/2018 | Dees, Jr. |
| 2009/0299482 A1 | 12/2009 | Metzger et al. |
| 2017/0035572 A1 | 2/2017 | Servidio |
| 2019/0091030 A1 | 3/2019 | Incavo |

SYSTEMS AND METHODS FOR CONVERTING A JOINT PROSTHESIS FROM A FIRST TYPE TO A SECOND TYPE IN-SITU

CROSS-REFERENCE TO RELATED APPLICATIONS

This application claims the benefit of the filing date of U.S. Provisional Patent Application No. 62/873,514, filed Jul. 12, 2019, the disclosure of which is hereby incorporated by reference.

BACKGROUND OF THE INVENTION

The current state of the art in knee replacement surgery offers orthopedic surgeons with a myriad of options to treat their patients, depending on the specific condition to be treated. The vast majority of knee replacement surgery is to treat arthritis of the knee, with trauma and bone cancer being exceptions. Knee replacement surgery to treat arthritis of the knee varies significantly depending on the state of disease progression.

The knee joint consists generally of three distinct regions, the medial tibiofemoral compartment, the lateral tibiofemoral compartment and the patellofemoral compartment. Arthritis of the knee can be limited to one compartment, for example the patellofemoral compartment or the medial tibiofemoral compartment. Conversely, arthritis can be found in two compartments simultaneously, for example the patellofemoral and medial tibiofemoral compartments. Finally arthritis can be found in all three aforementioned compartments.

Knee replacement surgery can be tailored to treat the specific condition diagnosed. For example, for patients with isolated compartmental disease, a partial knee replacement or partial knee arthroplasty ("PKA") procedure may be performed, such as unicompartmental knee replacement or patellofemoral joint replacement, which are well known and understood in the current state of the art. In patients with arthritis in all three compartments, a total joint knee replacement or total knee arthroplasty ("TKA") is performed, also well-known and understood in the current state of the art.

Patients who undergo primary knee replacement surgery, whether for a PKA or a TKA, can expect to undergo one or more revision procedures. The causes for revision surgery can vary from mechanical failure of the implant, infection of the joint, aseptic loosening of the implant, or joint instability due to the progression of disease. Continued arthritic changes of the joint over time often results in changes to the quality of the bone as well as deterioration of the strength and efficacy of the ligamentous structures. Deterioration of the ligaments of the knee can be a source of joint instability.

Ligamentous instability often requires implants with increased constraints to be implanted to compensate for the increased deficiency of the ligaments. As an example, a patient who undergoes a primary total knee replacement surgery may receive a cruciate retaining ("CR") implant, which is indicated when both collateral ligaments as well as the posterior cruciate ligament ("PCL") are intact and functional. The patient over time may develop mid-flexion instability and may be revised to a posterior stabilized ("PS") component whereby the function of the deteriorating PCL is substituted by an implant employing a cam and post design, well known and understood in the art. Said patient may also develop varus/valgus instability as a result of weakened or attenuated collateral ligaments and may alternatively be revised with a total stabilized ("TS") implant whereby a cam and post with increased constraint is used to augment the compromised collateral ligaments. Finally, in severe cases a TS implant may be insufficient to compensate for the total loss of function of the collateral ligaments. In such severe cases, a hinge implant may be indicated. Hinge implants are the most constrained of all knee systems and typically comprise femoral and tibial prostheses that are connected together via an axle which forms a hinge about which the artificial joint flexes and extends.

Amongst the many drawbacks associated with revision knee surgery are the loss of bone associated with the explantation of the prior components as well as the potential risks associated with increased surgical time due to the long and tedious process of implant removal. These drawbacks are most apparent in cases requiring a TS implant to be revised to a hinge implant due to joint instability. In many cases, TS femoral and tibial implants may exhibit solid cement fixation and may also be deemed to be in good anatomic alignment. However, due to collateral ligament instability, all of the TS implant's components may have to be explanted in favor of a hinge implant because none of the design characteristics of such TS components are compatible with the hinge implant. Further complicating the removal of a well fixed (cemented) TS implant is the fact that they are often used with intramedullary stems, both in the tibia and the femur, which are not easy to extract from the bone particularly without compromising the structure of the bone. Thus, further improvements are desirable.

BRIEF SUMMARY OF THE INVENTION

The present disclosure describes implant systems in which a TS implant can be converted to a hinge implant in situ without the TS implant being removed from the bone and at a fraction of the time typically required to revise a TS implant to a hinge implant. Preferably, the modular TS-to-Hinge conversion implant would be factory assembled in a TS configuration in order to make its use in the operating room identical to current TS implants. Meeting this preferred scenario is not without significant challenges. For example, the kinematics, spatial constraints and strength requirements for both TS and hinge applications are sufficiently distinct enough that addressing the design requirements for one often comes at the expense of the other. With respect to the surgeons' expectations and the patients' clinical needs, if a "convertible" TS-to-Hinge implant design were to be available, the performance requirements for each, whether in a TS mode or a Hinge mode should be virtually the same to each respective implant as a stand-alone component. In other words, TS-to-Hinge convertibility should not come at the expense of implant performance and/or durability, regardless of how easy the conversion may be. The devices, systems, and methods described herein address these potential pitfalls.

In one aspect of the present disclosure, a method of converting a joint prosthesis from a first type to a more constrained second type in situ, includes: removing a first modular component from a femoral component that was previously implanted onto a distal femur while the femoral component remains connected to the distal femur, the first modular component having a cam surface configured to articulate with a post of a first tibial assembly; and connecting an axle to the femoral component and to a second tibial assembly while the femoral component remains connected to the distal femur.

In another aspect of the present disclosure, a joint prosthesis system for converting a joint prosthesis from a first type to a more constrained second type in situ, includes a femoral component that has an articular side, a bone facing side, and medial and lateral condylar portions. The medial and lateral condylar portions at least partially define an intercondylar recess located therebetween and a transverse opening extending transverse to the articular side and bone facing side. The intercondylar recess intersects the transverse opening. The system also includes a first tibial assembly that has a tibial baseplate component and a post extending therefrom. Also included in the system is a first modular component separately formed from the femoral component and which is configured to connect thereto. The first modular component has a camming surface configured to articulate with the post of the first tibial assembly. The system further includes a second tibial assembly that has a tibial baseplate component and a head extending therefrom. The head defines an axle opening extending therethrough. An axle is configured to be received within the axle opening and transverse opening so as to connect the second tibial assembly to the femoral component.

In a further aspect of the present disclosure, a joint prosthesis system, includes a femoral component that has an articular side, a bone facing side, and medial and lateral condylar portions. The medial and lateral condylar portions at least partially define an intercondylar recess located therebetween and have a concave surface that extends in a mediolateral direction across the medial and lateral condylar portions. The system also includes a first tibial assembly that has a tibial baseplate component and a post extending therefrom. The system further includes a first modular component that has a camming surface configured to extend at least partially across the intercondylar recess when the first modular component is connected to the femoral component and to articulate with the post of the first tibial assembly. Also included in the system is a second modular component that has a first member and a second member. The first member has a convex surface corresponding to the concave surface of the femoral component. The second member extends from the first member and is configured to engage the first modular component so as to secure the first modular component to the femoral component.

In a yet further aspect of the present disclosure, a joint prosthesis system, includes a femoral component that has an articular side, a bone facing side, and medial and lateral condylar portions. The medial and lateral condylar portions at least partially defining an intercondylar recess located therebetween and having a first concave surface extending in a mediolateral direction across the medial and lateral condylar portions. The system also includes a first modular component that has a second concave surface and is connectable to the femoral component such that, when the first modular component is connected to the femoral component, the first and second concave surfaces come together to form a transverse opening extending in the mediolateral direction. The system further includes a first tibial assembly that has a tibial baseplate component and a head extending therefrom. The head defines an axle opening extending therethrough. An axle is configured to be received within the transverse opening and axle opening so as to connect the tibial assembly to the femoral component.

BRIEF DESCRIPTION OF THE DRAWINGS

The features, aspects, and advantages of the present disclosure will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart, and the term "distal" means more distant from the heart. The term "inferior" means toward the feet, and the term "superior" means toward the head. The term "anterior means toward the front of the body or the face, and the term "posterior" means toward the back of the body. The term "medial" means toward the midline of the body, and the term "lateral" means away from the midline of the body. Also, as used herein, the terms "about," "generally" and "substantially" are intended to mean that deviations from absolute are included within the scope of the term so modified.

Figure 1A:
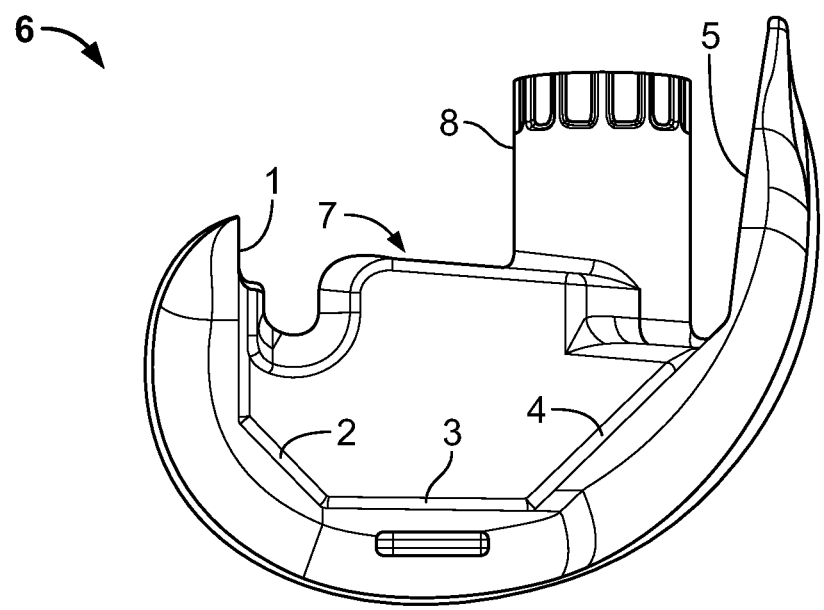
FIG. 1A is a side elevational view of a first prior art femoral component.

FIG. 1A depicts a prior art TS femoral component 6 that includes a bone facing side and an articular side. The bone facing side includes a plurality of intersecting bone facing surfaces 1-5. As shown, a typical TS femoral component 6 includes five of such intersecting bone facing surfaces. When femoral component is implanted, these bone facing surfaces 1-5 interface with corresponding resected surfaces of a distal femur. In this regard, distal femurs are commonly resected so as to exhibit five planar intersecting surfaces which are commonly understood as an anterior resection, posterior resection, distal resection, anterior chamfer resection, and posterior chamfer resection.

Since TS femoral component 6 is ordinarily indicated for circumstances where a patient's collateral ligaments exhibit some laxity such that some level of constraint is required to stabilize the artificial joint, TS femoral component 6 includes a cam box 7 and stem boss 8. Cam box 7 extends superiorly from bone contacting surfaces 1-4 and contains a cam surface (not shown) within an interior thereof at the articular side of the femoral component 6. Such cam surface articulates with a post of a tibial insert, such as the tibial insert 200 depicted in FIG. 4D and described further below. This cam-post mechanism provides functionality ordinarily performed by the cruciate ligaments, such as femoral rollback, which are typically sacrificed in TS procedures, and also helps stabilize the artificial joint in the face of collateral ligament instability. Further support is provided to femoral component by way of stem boss 8 and a stem (not shown) connected to stem boss 8. PS femoral components are similar to TS femoral component 6 except that PS femoral components typically do not include intramedullary stems.

Figure 1B:
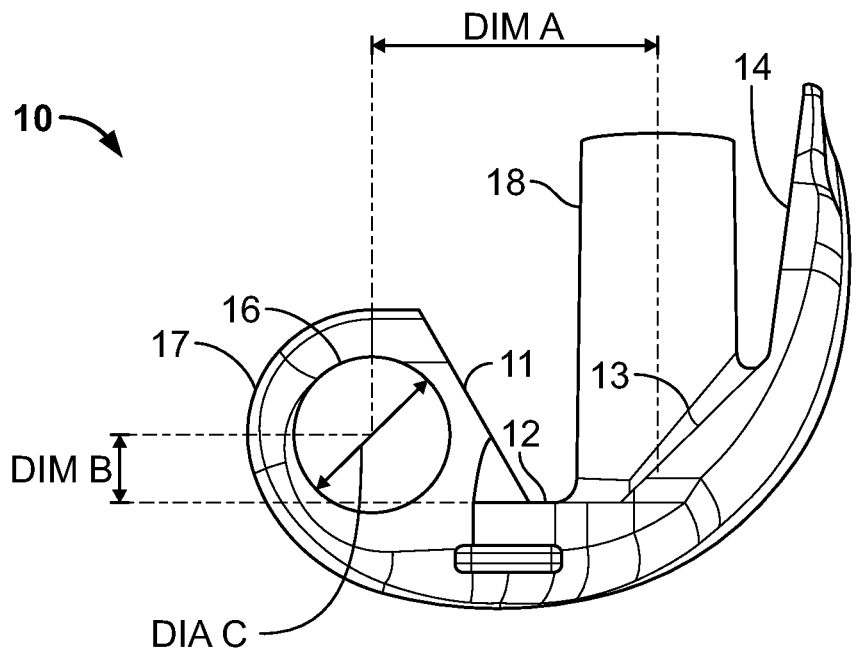
FIG. 1B is a side elevational view of a second prior art femoral component.

FIG. 1B depicts a prior art hinge femoral component 10 which includes a bone contacting side and an articular side. The bone contacting side includes a plurality of intersecting bone facing surfaces 11-14. However, unlike the TS femoral component 6, hinge femoral component 10 is shown as having four of such surfaces rather than five. This is to help create enough space at a posterior aspect of femoral component 10 to accommodate a transverse opening 16. Transverse opening 16 passes through femoral component 10 in a mediolateral direction between the bone facing and articular sides and is sized to accommodate an axle of a tibial assembly. An exemplary hinge knee assembly and corresponding femoral component, axle, and tibial assembly are disclosed in U.S. Publication No. 2017/0035572 ("the '572 Publication"), the disclosure of which is hereby incorporated by reference herein in its entirety. It is noted that, while hinge femoral component 10 also includes a stem boss 18, femoral component 10 does not include a cam box since the axle that connects to femoral component 10 provides the appropriate constraint, rather than a cam-post mechanism like that of TS femoral component 6.

The prior art femoral components 6 and 10, as described above, include two separate features which are utilized to constrain the artificial joint, the first being cam box 7 for the cam-post mechanism, and the second being the transverse opening 16 and corresponding hinge axle. It is particular noted that a hinge axle undergoes significant stress over the lifetime of use and, therefore, has a large diameter for strength. However, this comes at the cost of space which is not in abundance on a femoral component. Attempts to make the axle smaller in an effort to be more bone preserving have resulted in designs with higher clinical failure rates. Thus, developing a femoral component that can be converted in situ from a TS configuration to a hinge configuration without removal of the same comes with particular challenges. For example, when the axle location (DIM A & B) is superimposed on the TS femoral component 6, a posterior wall 17, such as that shown in FIG. 1B, results but is thinned out relative to that of femoral component 10, thus potentially negatively affecting the strength of the resulting femoral component when loaded posteriorly, such as would occur in deep flexion, for example as in rising from a chair. Moreover, as mentioned above, TS femoral component 6 has more intersecting bone facing surfaces than hinge femoral component and is, therefore, more bone preserving. While such additional bone removal is acceptable in a hinge surgery scenario, such is not typically the case in a TS scenario. Thus, the design challenges involve competing design features. The devices, systems, and methods described below solve these design challenges and more.

FIGS. 2A-7C depict a system for converting a joint prosthesis from a first type to a more constrained second type in situ. The system generally includes a femoral component 20, TS modular components (40, 50), hinge modular components (60, 70), a first tibial assembly (200, 210), and a second tibial assembly 80.

Figure 2A:
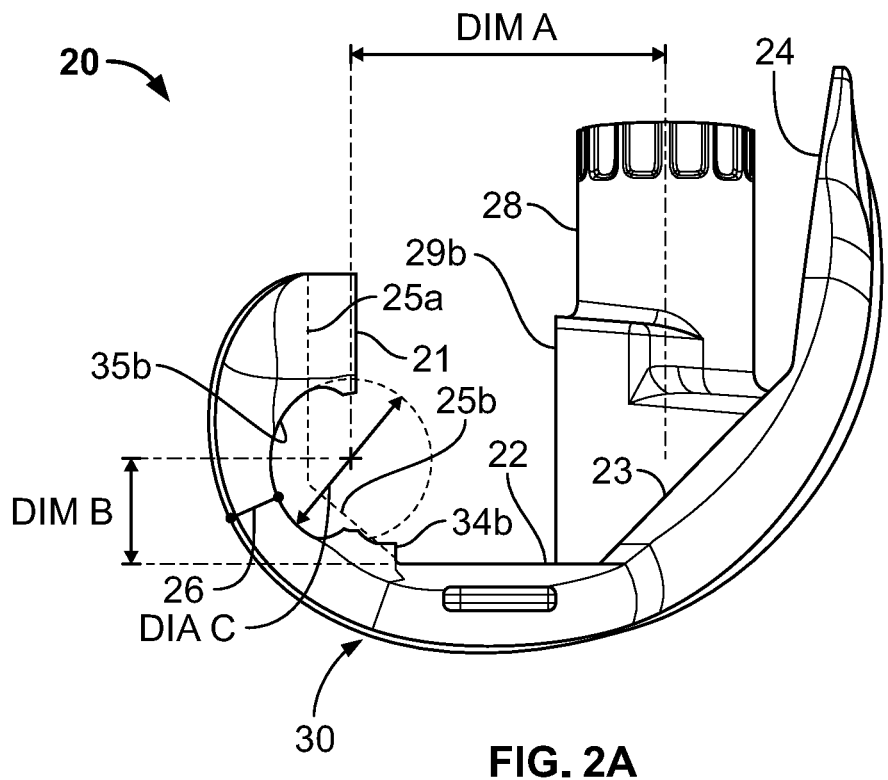
FIG. 2A is a side elevational view of a femoral component according to an embodiment of the present disclosure.
Figure 2B:
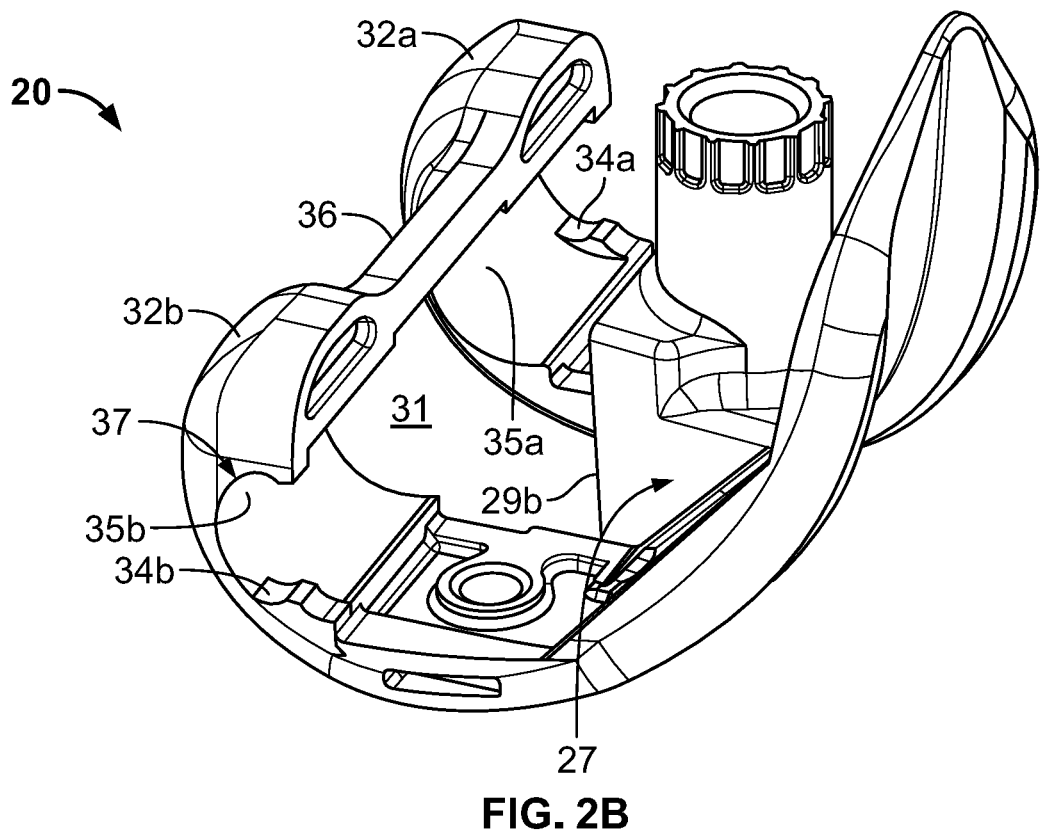
FIG. 2B is a perspective view of the femoral component of FIG. 2A.

FIGS. 2A-2B depict a base femoral component 20 according to an embodiment of the present disclosure. Femoral component 20 generally includes a bone facing side, an articular side, lateral and medial condylar portions 32a-b, and a strut 36. Lateral and medial condylar portions 32a-b are separated by an intercondylar recess or notch 31. Strut 36 is connected to lateral and medial condylar portions 32a-b and extends across intercondylar recess 31. In the embodiment depicted, strut 36 connects to lateral and medial condylar portions 32a-b at respective ends thereof.

The bone facing side includes a plurality of intersecting inner bone facing surfaces 21-24, a partial hinge housing 37, interlocking features 34a-b, a partial cam box or base 27, and a stem boss 28.

The plurality of intersecting bone facing surfaces 21-24 are generally planar surfaces that correspond to resected surfaces of a distal femur. While such surfaces 21-24 are generally planar, they can include depressions and the like for receipt of bone cement, for example. However, their profiles are each as a planar surface to match a corresponding planar resected surface of a femur. In the embodiment depicted, femoral component 20 includes four bone facing surfaces 21-24 that correspond to four resected surfaces of a femur. Femoral component 20 may, however, have five of such inner surfaces, although femoral component preferably includes four inner bone facing surfaces 21-24 in order to accommodate partial hinge housing 37. In other embodiments, the bone facing side may have only three bone facing surfaces which would also accommodate partial hinge housing 37. However, four inner bone facing surfaces 21-24 is preferred over three because it allows for less bone removal than three inner surfaces while providing for sufficient space for partial hinge housing 37.

While femoral component 20 includes four inner bone facing surfaces 21-24, it should be noted that inner surface 25b (see FIG. 2A), which corresponds to surface 2 of TS femoral component, has been eliminated in order to accommodate partial hinge housing 37 and interlocking features 34a-b. Moreover, inner bone facing surface 25b (see FIG. 2A), which corresponds to first inner surface 1 of femoral component 6, has been replaced by first inner bone facing surface 21. Bone facing surface 21 is shifted parallel and anterior to surface 25a. However, while this results in more bone removed from a distal femur as compared to femoral component 6, such additional bone removed by the substitution of surface 21 for surface 25a is consistent with what would be removed for accommodation of an augment block (not shown) that is commonly used in TS revision procedures to address posterior-condylar bone loss. Thus, the additional bone that would be removed to accommodate femoral component 20 would not go beyond commonly accepted parameters for TS procedures.

Partial hinge housing 37 extends from the bone facing side into femoral component 20 toward the articular side. In particular, hinge housing 37 extends through first inner surface 21, which is a surface that extends in a superior-inferior direction. Hinge housing 37 is defined by a concave surface that 35 extends across lateral and medial condylar portions 32a-b. However, concave surface 35 is interrupted by intercondylar recess 31 such that concave surface 35 forms a lateral concave surface 35a and medial concave surface 35b. Such concave surfaces 35a-b, in the embodiment depicted, are semi-cylindrical, and more particularly hemi-cylindrical. However, in some embodiments concave surfaces 35a-b may form less or more than half of a cylinder.

As shown in FIG. 2A, femoral component 20 maintains the same axle housing size (DIA. C in FIGS. 1B and 2A) and location (DIMs. A and B in FIGS. 1B and 2A) as hinge femoral component 10. However, femoral component 20 does not require as much bone removal as femoral component 10 because the axle housing is composed of two halves, the first half being partial housing 37 which is integral to the femoral component and described above, and the second half, which is not present while in a TS configuration, is comprised of a modular component 60, described below. However, it is noted that a thickness 26 of femoral component between concave surface 35 and the articular side of femoral component is diminished relative to femoral component 10. However, whatever strength is lost due to this reduction in thickness 26 is compensated for by making a modular box component 50 (see FIG. 3B) a stressed member to share the load, as described further below.

Interlocking features 34a-b are located at lateral and medial flanks of partial hinge housing 37 and extend superiorly from femoral component 20. In this regard, interlocking features 34a-b are protrusions that form abutments for modular components disposed within partial hinge housing 37, as described further below.

Partial cam box or base 27 extends superiorly from the bone facing side of femoral component 20. In particular, cam box 27, as shown, interrupts and extends from second and third inner surfaces 22, 23. Partial cam box 27 is located at an anterior extent of intercondylar recess 31 and terminates well before reaching first inner surface 21 such that a rectangular shaped gap extends between first inner surface 21 and partial cam box 27, as best shown in FIG. 2A. Partial cam box 27 includes a plurality of box walls 29 extending posteriorly from a posterior end of partial box 27 (see FIGS. 2A, 2B, 4B, and 4C). In particular, a first, second, and third wall 29a-b intersect each other so as to form a generally rectangular recess therein with third wall 29c forming a ceiling of partial box 27.

Stem boss 28 extends superiorly from partial cam box 27 and includes an opening therein for receipt of a modular stem (not shown). However, in some embodiments, stem boss 28 may instead be an integral full-length stem incorporated into the structure of femoral component 20. The bone facing side may include a porous material, such as titanium foam and the like for promoting bone ingrowth, such as when femoral component 20 is press-fit to a femur. However, the bone facing side may instead include solid surfaces for instances in which femoral component 20 is cemented to a femur.

Figure 3A:
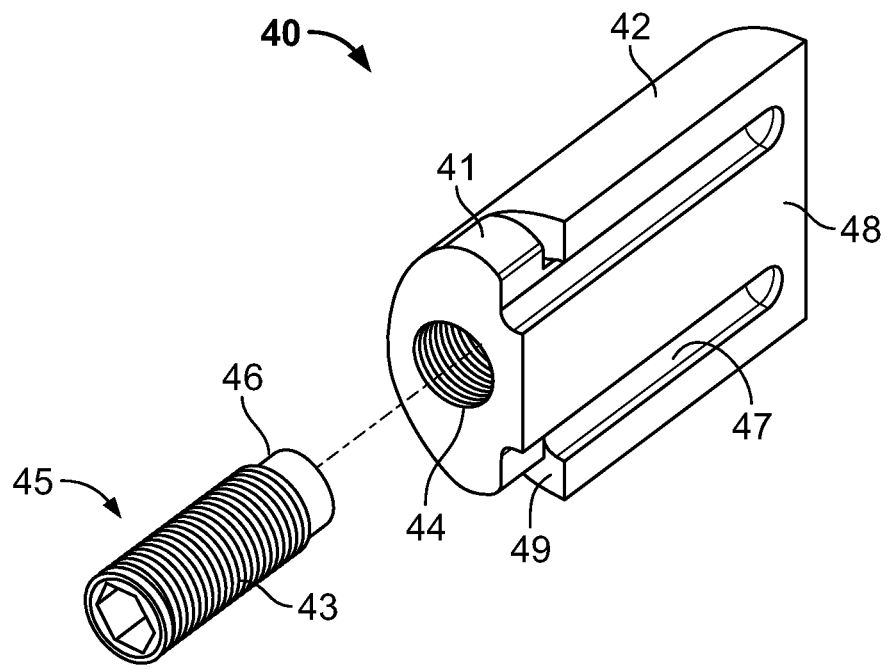
FIG. 3A is a perspective view of a box locking housing according to an embodiment of the present disclosure.
Figure 3B:
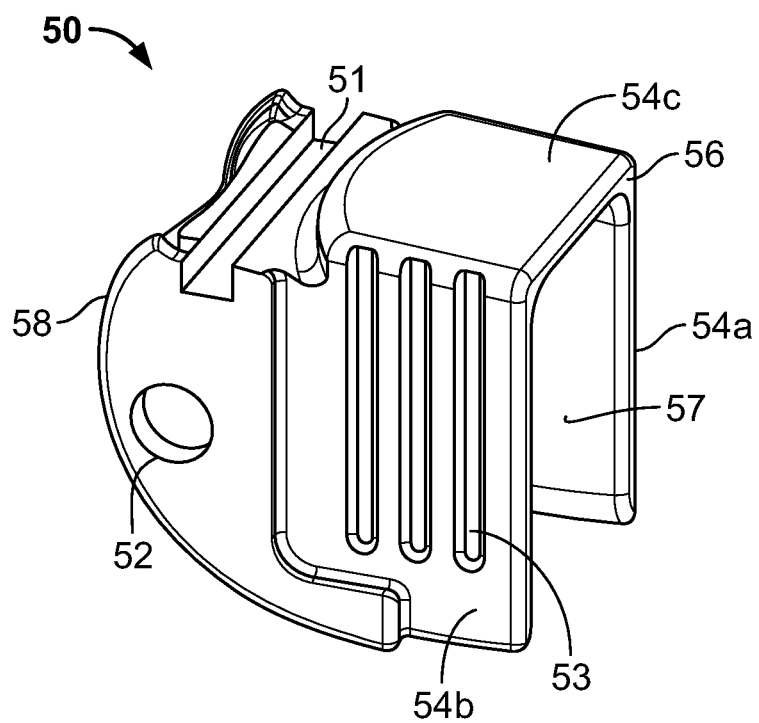
FIG. 3B is a perspective view of a modular box member according to an embodiment of the present disclosure.

FIGS. 3A and 3B depict the TS modular components which include a box locking housing 40 and a modular box 50. These modular components are utilized in conjunction with base femoral component 20 to create a TS mode femoral component 20'. Box locking housing 40 has a semi-cylindrical body such that one side thereof has a convex surface 42 and another side thereof has a planar surface 48. Box locking housing 40 is configured to be received by partial hinge housing 37. In this regard, convex surface 40 is curved to correspond with one of concave surfaces 35a-b. In addition, planar surface 48 is configured to be an extension of first inner bone facing surface 21 when box locking housing 40 is engaged to femoral component 20. Thus, planar surface 48 is also a bone facing surface and includes depressions or grooves 47 therein which are configured to receive bone cement.

Box locking housing 40 also has a first end and a second end. The first end includes an interlocking feature 41 which is a section of reduced cross-sectional dimension from the remainder of the box locking housing's body such that this reduced shape/size forms abutment shoulders 49. In this regard, interlocking feature 41 is configured to be received within a space between interlocking feature 34a or 34b and an end of hinge housing 37. The abutment shoulders 49 are configured to abut interlocking feature 34a-b. Thus, it should be noted, that box locking housing 40 is loaded into hinge housing 37 via intercondylar recess 31. As such, box locking housing 40 has a length that is smaller than a mediolateral width of intercondylar recess 31. The second end of box locking housing 40 is generally planar and is configured to abut walls of modular box 50 when assembled with femoral component 20. Box locking housing 40 defines a threaded opening 44 spanning the entire length thereof, and includes a screw 45 with a threaded shaft 43 and a non-threaded post 46 at an end of threaded shaft 43.

Modular box 50 generally includes a plurality of box walls 54 and a cam surface 59. In particular, modular box 50 includes three box walls 54a-c in which first and second box walls 54a-b are opposed to each other, and third box wall 54c extends transverse to first and second walls 54a-b and connects the two to create a rectangular structure with an open inferior end. Cam surface 59, as shown in FIG. 4B, is located within an interior of box 50 and spans between first and second box walls 54a-c. Cam surface 59 is configured to articulate with a post of a tibial assembly. Modular box 50 includes an anterior end and a posterior end. The anterior end includes an abutment face 56 formed by the ends of box walls 54*a-c*. Abutment face 56 is substantially planar. At the posterior end, first and second box walls 54*a-b* form convexly curved ends or wings 58 so as to match a curvature of condylar portions 32*a-b*. First and second box walls 54*a-b* each include an aperture 52 configured to receive the non-threaded post 46 of screw 45. In addition, first and second box walls 54*a-b* each include elongate grooves 53 that extend in a superior-inferior direction. Such grooves 53 allow for the interdigitation of bone cement to help secure box 50 to bone. However, the travel of elongate grooves 53 in the superior-inferior direction allows box 50 to be easily removed from femoral component 20, even when cemented, during a transition to a hinge configuration as such grooves 53 extend in the same direction of travel for removal of box component 50. Third wall 54*c* includes a mating slot 51 that extends in a mediolateral direction and is configured to receive strut 36 of femoral component.

Figure 4A:
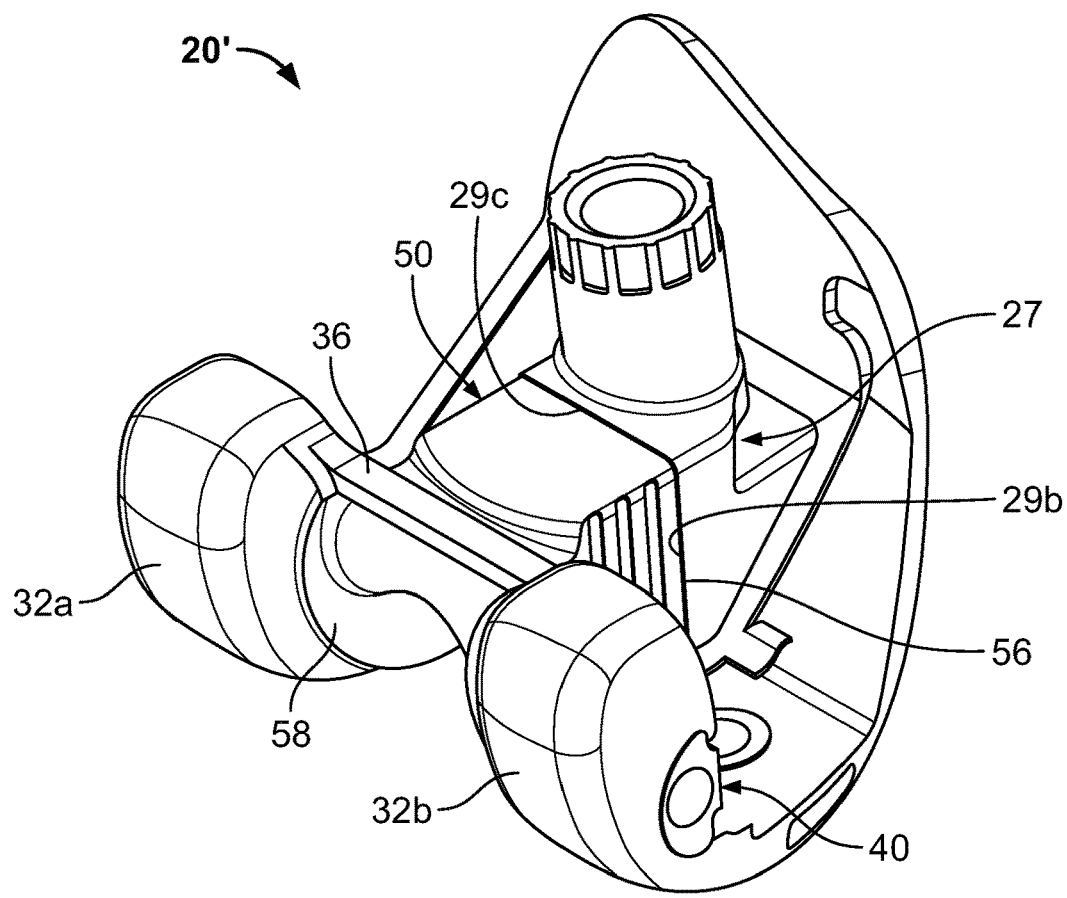
FIG. 4A is a perspective view of an assembly according to an embodiment of the present disclosure including the femoral component of FIG. 2A, the box locking housing of FIG. 3A, and modular box member of FIG. 3B.
Figure 4B:
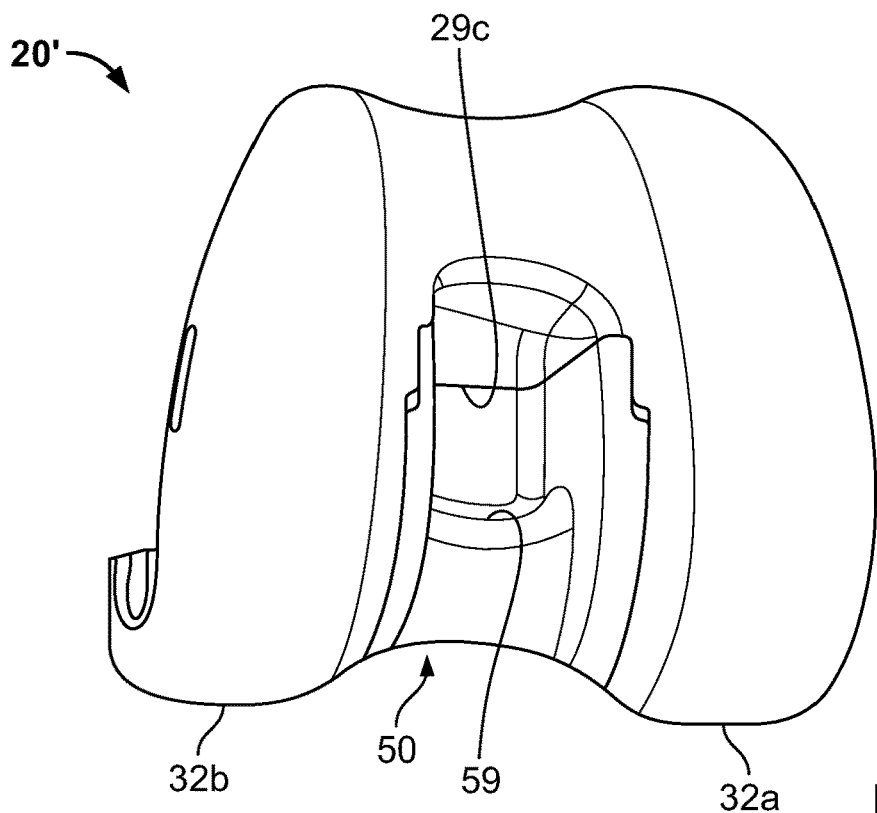
FIG. 4B is a bottom view of the assembly of FIG. 4A.
Figure 4C:
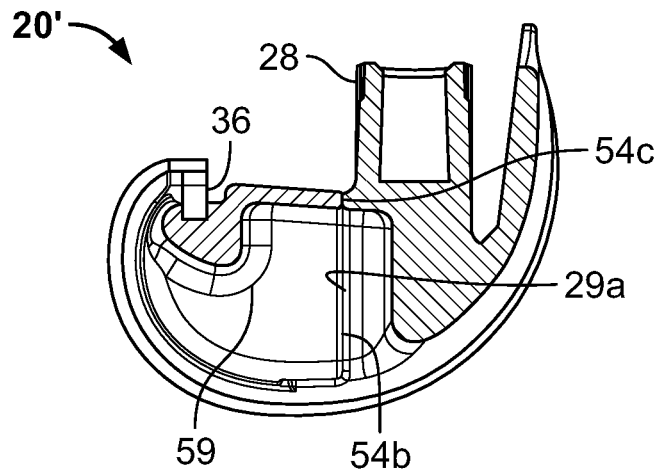
FIG. 4C is a side cross-sectional view of the assembly if FIG. 4A taken along a midline thereof.

FIGS. 4A-4C depict a TS configured femoral component 20'. TS configured femoral component 20' includes femoral component 20, modular box 50, and a pair of modular box housings 40. As shown, modular box 50 is positioned within intercondylar recess 31 such that the anterior end of box walls 54*a-c* abut corresponding partial box walls 29*a-c* of partial cam box 27. In addition, convexly curved posterior ends 58 of first and second walls 54*a-b* engage with and curve along with the curvature of lateral and medial condylar portions 32*a-b*, as best shown in FIG. 4A. Also, strut 36 is positioned within mating slot 51.

First and second modular box housings 40*a-b* flank partial cam box 50 and are positioned within partial axle housing 37. In this regard, convex surfaces 42 of modular box housings 40*a-b* correspondingly engage concave surfaces 35*a-b* of their respective lateral and medial condylar portions 32*a-b*. Abutment shoulders 49 of box locking housings 40 abut interlocking features 34*a-b* of femoral component 20 while interlocking features 41 extend between interlocking features 34*a-b* and concave surfaces 35*a-b*. Planar surfaces 48 of housings 40*a-b* also lay flush with first bone facing surface 21 of femoral component so as to extend first bone facing surface 21. A locking screw 45 is positioned within the threaded opening 44 of each box housing 40*a-b* such that non-threaded post 46 extends from the first end 43 thereof and into an aperture 52 of a respective box wall 54*a-b* to secure box 50 to femoral component 20.

As mentioned above, thickness 26 of femoral component 20 is lessened compared to that of femoral component 10. To help reduce stress in this region, posterior compressive load experienced in deep flexion is transferred through modular box 50 via strut 36, which is coupled to mating slot 51, and the anterior abutment surface 56 formed by box walls 54*a-c* being in contact with corresponding walls 29*a-c* of femoral component 20. In this regard, loads applied to condylar portions 32*a-b* are at least partially transferred through box locking housing 40, screws 45, apertures 52, and finally through the length of box 50 onto integral base 27. Therefore, modular box 50 contains multiple points of load transfer.

Figure 4D:
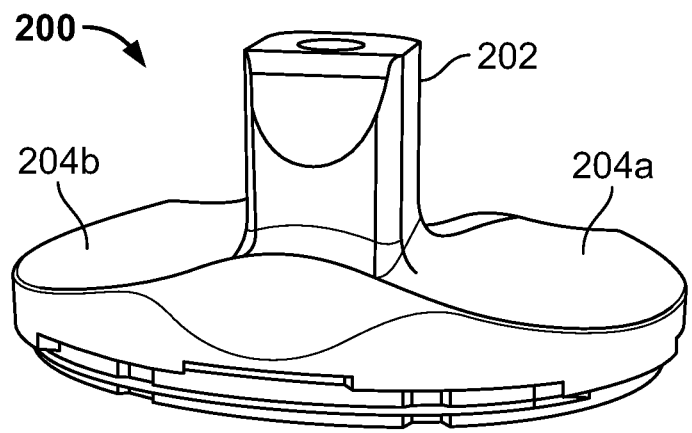
FIG. 4D is a perspective view of a tibial insert according to an embodiment of the present disclosure.
Figure 4E:
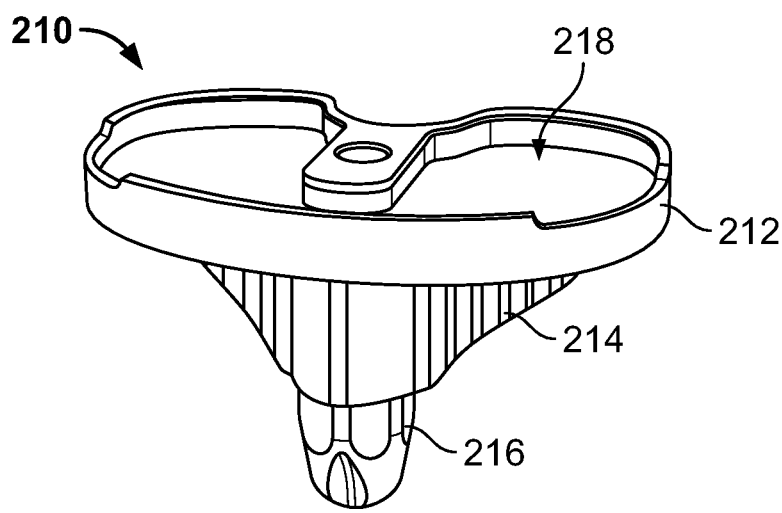
FIG. 4E is a perspective view of a tibial baseplate according to an embodiment of the present disclosure.

FIGS. 4D and 4E depict a first tibial assembly or TS tibial assembly. TS tibial assembly includes a tibial insert 200 and baseplate component 210. Tibial insert 200 generally includes an articular side that is comprised of lateral and medial condyles 204*a-b* which are concave surfaces configure to articulate with femoral component 20. In addition, tibial insert 200 includes a post 202 extending therefrom. Post 202 is configured to be received within intercondylar recess 31 of femoral component 20 and to articulate with cam surface 59 in order to help prevent anterior subluxation and to provide functionality lost due to the sacrifice of the cruciate ligaments. Insert 200 is preferably made from a biocompatible polymer material, such as an ultra-high molecular-weight polyethylene (UHMWPE), for example.

Baseplate component 210 includes a baseplate 212, keels 214, and stem portion 216. Keels 214 and stem portion 216 extend inferiorly from baseplate 212. Baseplate 212 includes a superior tray 218 configured to receive tibial insert 200.

Figure 5A:
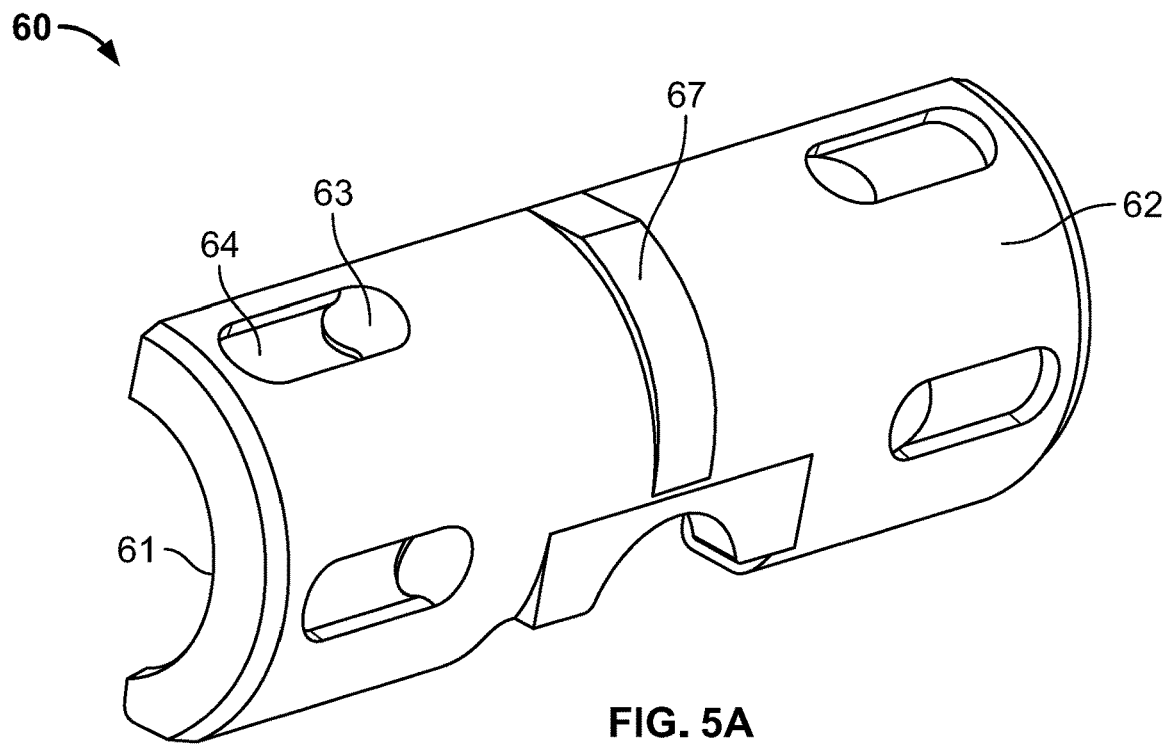
FIG. 5A is a perspective view of a hinge housing component according to an embodiment of the present disclosure.
Figure 5B:
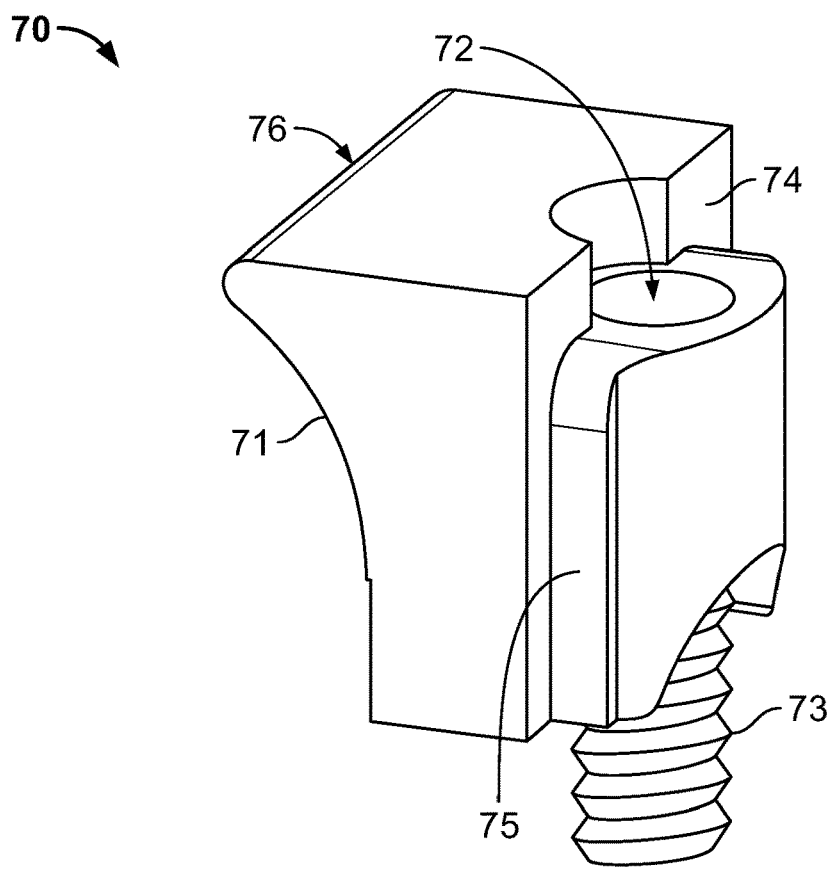
FIG. 5B is a perspective view of a locking wedge according to an embodiment of the present disclosure.

FIGS. 5A and 5B depict the hinge modular components which include a hinge housing component 60 and locking wedge or locking block 70. As indicated above, the hinge axle housing comprises two portions, the first portion is the concave surface integral 35 to femoral component 20. The second portion is modular hinge housing component 60. Modular hinge housing component 60 includes an inner concave surface 61 and an outer convex surface 62 concentric to first concave surface 61. Outer convex surface 62 includes a rib 67 extending transverse to a length of component 60. Such rib 67 is configured to be received within a corresponding groove of locking wedge 70, as described in more detail below. Concave surface 61 in the embodiment depicted, is semi-cylindrical, and more particularly hemi-cylindrical. However, in some embodiments concave surface 61 may form less or more than half of a cylinder. Housing component 60 also includes a plurality of apertures 63 and a plurality of grooves 64 each intersecting a corresponding one of such apertures 63. Apertures 63 allow bone cement to be delivered therethrough, as described below, and grooves 64 are interlocking features for the bone cement to secure housing component 60 to bone.

Locking wedge or locking block 70 is used to secure hinge housing component 60 to femoral component 20. Locking wedge 70 includes a body 76 that has a concave surface 71 which matches outer convex surface 62 of housing component 60. In this regard, concave surface 71 has a groove 77 extending along the curvature of surface 71 and is configured to receive rib 67, as best shown in the cross-section of FIG. 6C. Body 76 also includes an abutment surface 74 disposed opposite concave surface 71 for abutting surface of partial box 27. A protrusion 75 extends from abutment surface 74 and has a cross-sectional dimension smaller than that of body 76 such that protrusion 75 can be received within the recess formed by partial box walls 29*a-c*. In this regard, protrusion 75 centralizes as well as stabilizes locking wedge 70 to allow distal-proximal translation of the locking wedge 70 while preventing medial-lateral shift of said locking wedge 70. Locking wedge 70 further includes a threaded opening 72 extending in a superior-inferior direction entirely through protrusion 75. Threaded hole 72 is configured to receive wedge locking screw 73.

Figure 6A:
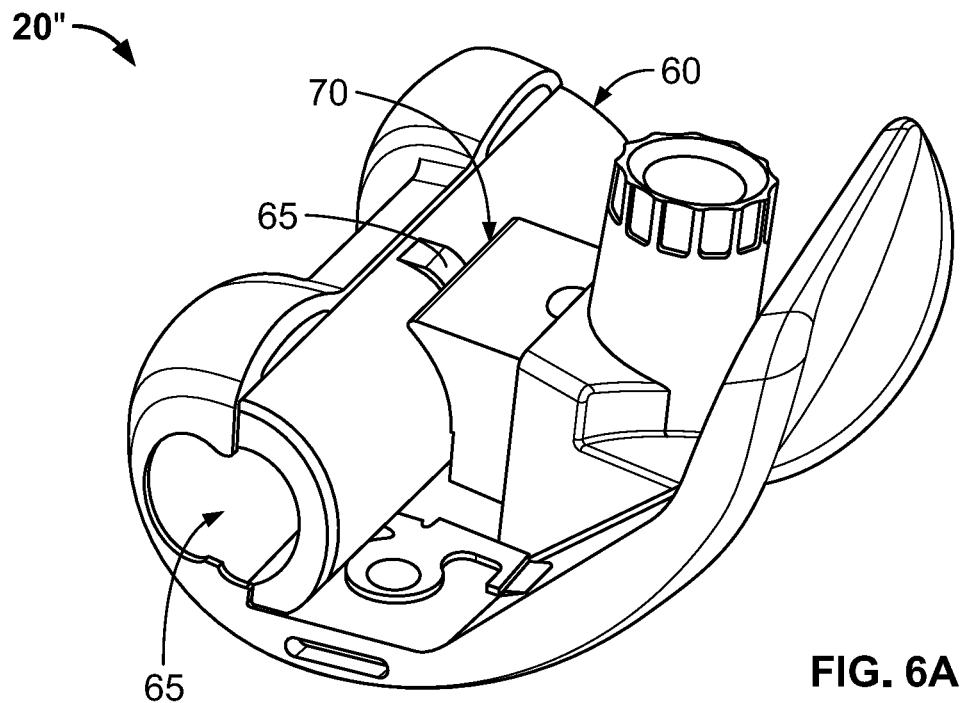
FIG. 6A is a perspective view of an assembly according to another embodiment of the present disclosure including the femoral component of FIG. 2A, the hinge housing component of FIG. 5A, and locking wedge of FIG. 5B.
Figure 6B:
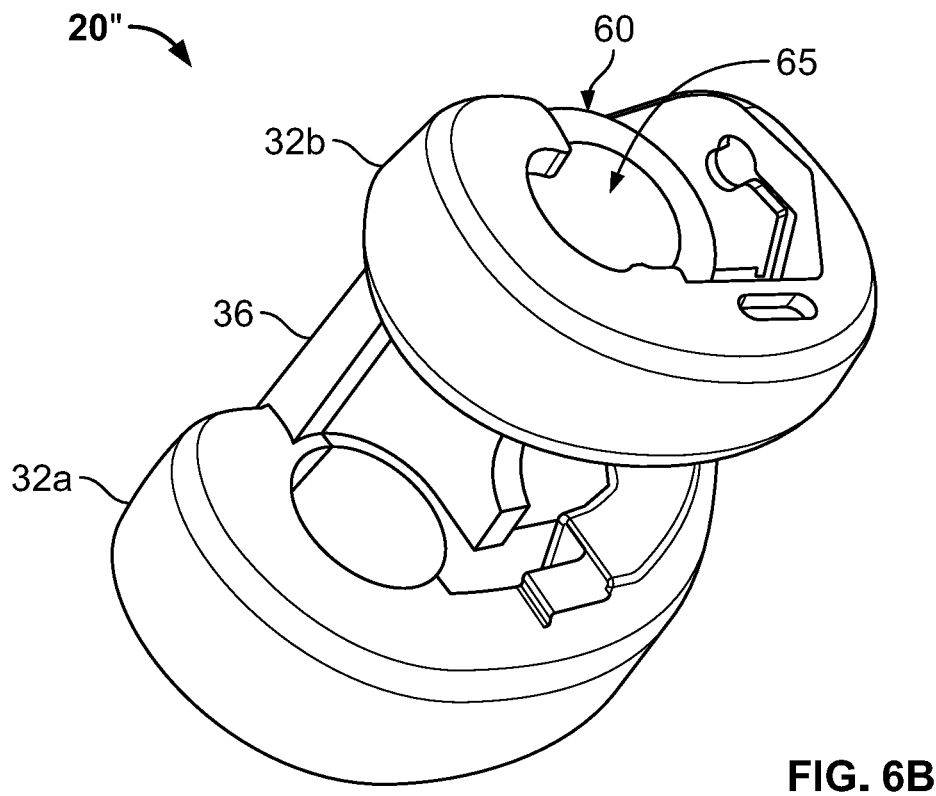
FIG. 6B is a perspective view of the assembly of FIG. 6A.
Figure 6C:
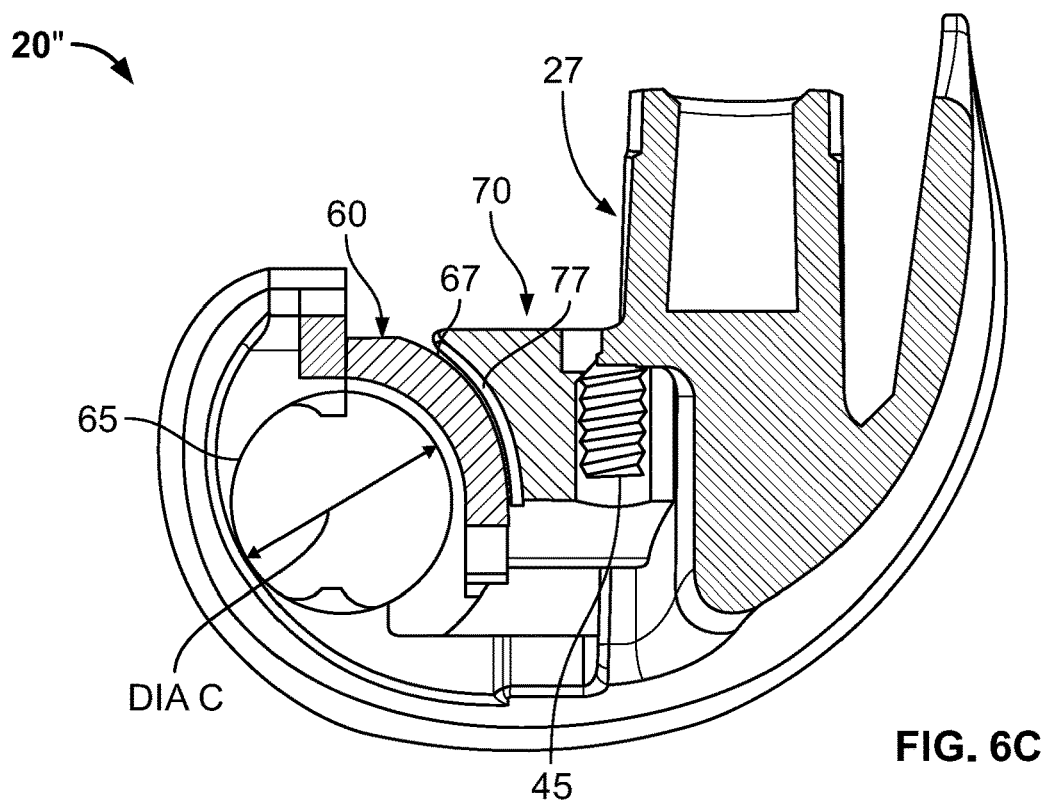
FIG. 6C is a side cross-sectional view of the assembly of FIG. 6A taken along a midline thereof.

FIGS. 6A-6C depict a hinge configured femoral component 20". Hinge configured femoral component 20" includes femoral component 20, modular hinge housing 60, and a locking wedge 70. As shown, hinge housing component 60 is positioned opposite partial hinge housing 37 such that concave surfaces 35 and 61 come together to form a transverse opening 65. Transverse opening 65 is generally cylindrical and is configured to receive an axle and corresponding bushings of a tibial assembly, as described below. In this regard, transverse opening 65 forms a diameter (DIA. C of FIG. 6C) which is identical in size and location to that of FIG. 1B thereby ensuring transverse opening 65 can accommodate a robust axle. Also, as best shown in FIGS. 6A and 6C, locking wedge 70 is positioned within a gap between partial box 27 and hinge housing component 60 such that protrusion 75 is positioned within box walls 29*a-c* of partial box 27 and concave surface 71 contacts convex surface 62 of housing component 60. In addition, rib 67 of housing 60 is received within groove 77 of wedge 70, as best shown in FIG. 6C, so as to constrain housing 60 from mediolateral movement. Locking screw 73 secures locking wedge to femoral component 20.

Figure 6D:
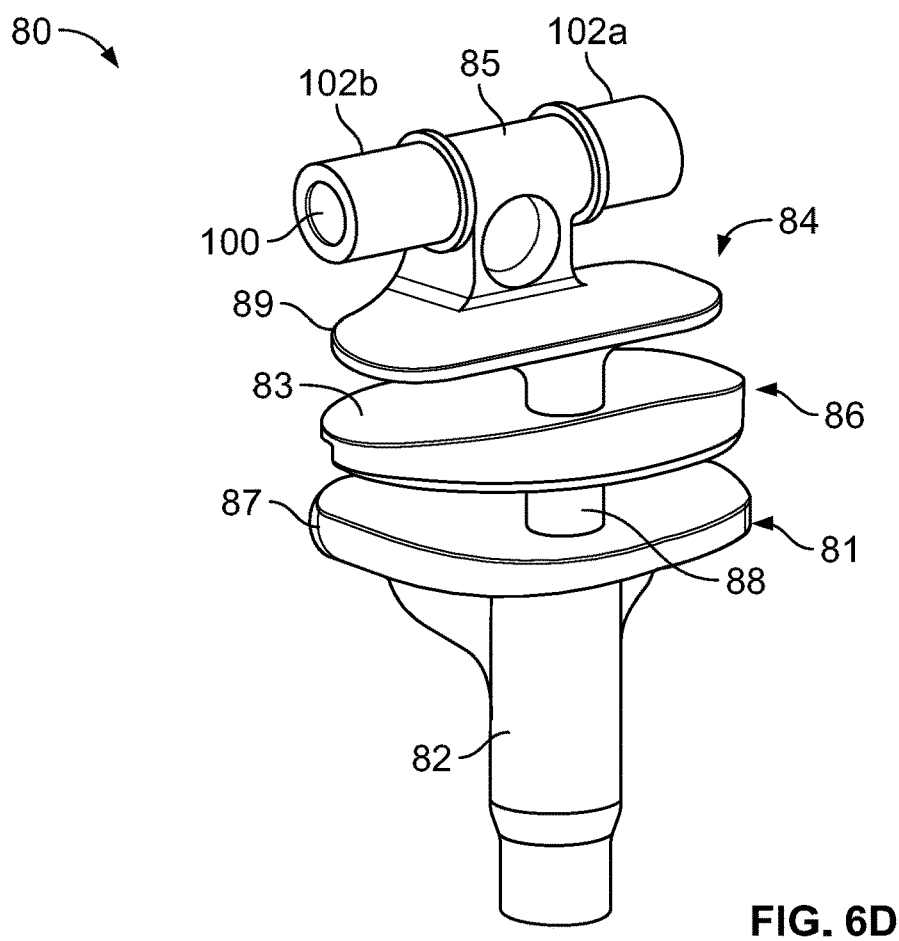
FIG. 6D is a perspective view of a tibial assembly according to an embodiment of the present disclosure.

FIG. 6D depicts a second tibial assembly or hinge tibial assembly 80. Hinge tibial assembly 80 generally includes a baseplate component 81, tibial insert 86, bearing component 84, axle bushings 102a-b, and a bearing shaft bushing (not shown). Examples of such components can be found in the heretofore referenced '572 Publication. Baseplate component 81 includes a stem portion 88 and baseplate 87. An opening extends through baseplate 87 and into stem portion 88.

Tibial insert 86 includes a concave articular surface 83 and a through-opening. Bearing component 84 includes a bearing plate 89, bearing shaft 88 extending from bearing plate 89, and a head 85 extending superiorly from bearing plate 89. Head 85 includes an axle opening extending therethrough in a mediolateral direction which is configured to receive the axle 100. Bushings 102a-b are made of polymer material and receive the portions of axle 100 not received within head 85, as shown in FIG. 6D. Such bushings 102a-b prevent metal-on-metal rubbing during use. In the embodiment depicted, bearing plate 89 is convexly curved so that it can articulate with concave surface 83 of tibial insert 86. However, in other embodiments, femoral component 20 may directly articulate with tibial insert 86. Thus, in such embodiments bearing component 86 may not include bearing plate 89.

Figure 6F:
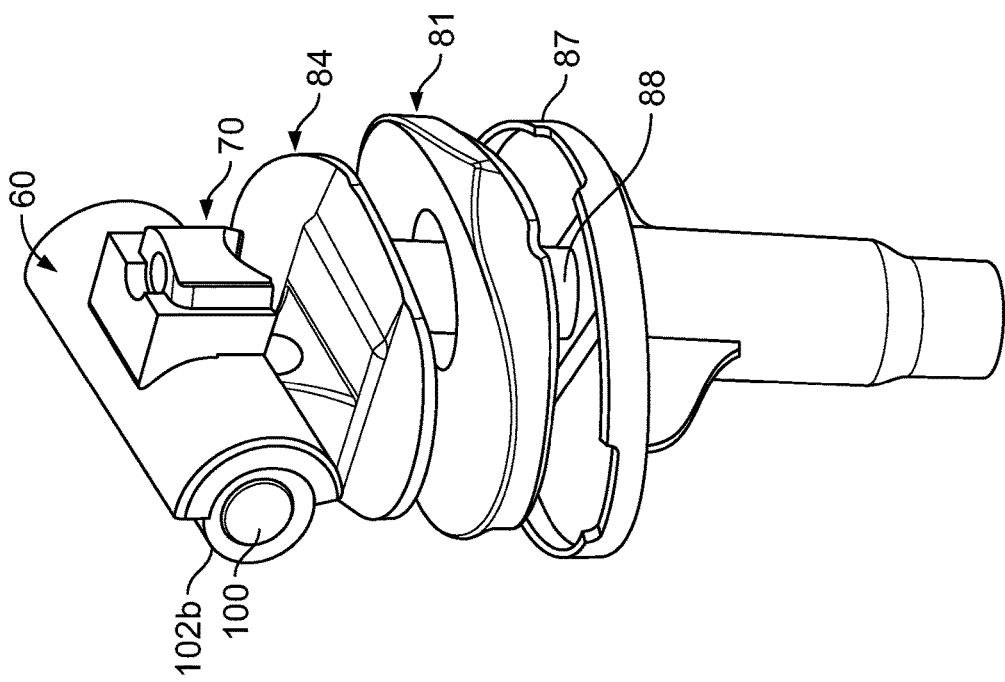
FIG. 6F is a perspective view of a partial hinge implant assembly including the hinge housing component of FIG. 5A, locking wedge of FIG. 5B, and tibial assembly of FIG. 6D.
Figure 6E:
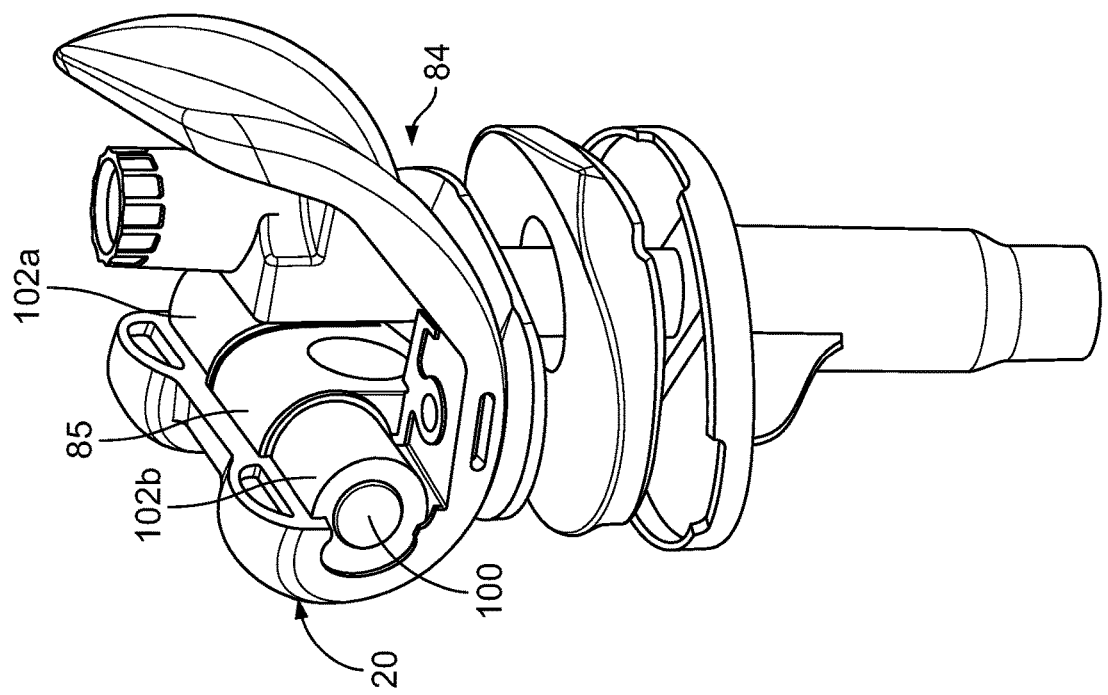
FIG. 6E is a perspective view of a partial hinge implant assembly including the femoral component of FIG. 2B and tibial assembly of FIG. 6D.

FIGS. 6E and 6F depict hinge tibial assembly 80 assembled with hinge configured femoral component 20". In this regard, tibial insert 86 is connected to baseplate 81 while bearing shaft 88 extends from bearing plate 89 and through both tibial insert 86 and baseplate 81 and into the opening thereof such that bearing plate 89 rests on tibial insert 86. Head 85 extends through intercondylar recess 31 such that the axle opening aligns with transverse opening 65. Axle 100 is positioned within transverse opening 65 and the axle opening so as to connect femoral component to tibial assembly 80. Moreover, bushings 102a-b are positioned over axle and between femoral component 20 and housing 60 so as to prevent metal-on-metal articulation. Femoral component 20" and tibial assembly 80 articulate in flexion and extension relative to each other about an axis defined by axle 100.

Figure 7A:
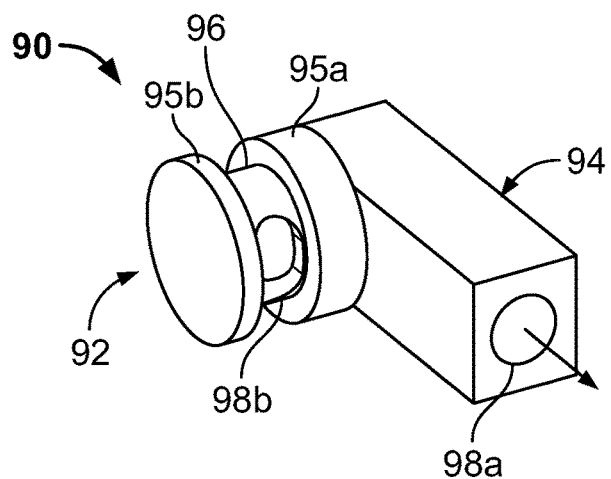
FIG. 7A is a perspective view of a cement nozzle according to an embodiment of the present disclosure.
Figure 7B:
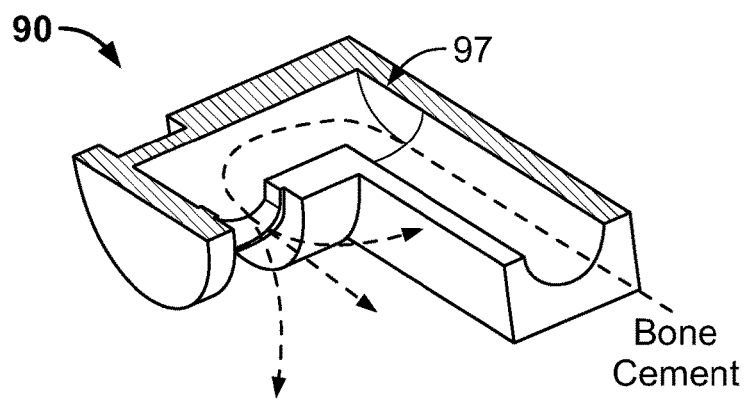
FIG. 7B is perspective cross-sectional view of the cement nozzle of FIG. 7A taken along a midline thereof.

FIGS. 7A and 7B depict a disposable bone cement nozzle 90 that can be connected to a cement applicator device (not shown), such as a standard bone cement gun. Such nozzle 90 is particularly configured to deliver bone cement around modular axle housing 60 while femoral component 20 remains attached to a femur in order to help secure such element to the bone after conversion from TS configured femoral component 20' to hinge configured femoral component 20". In this regard, cement nozzle 90 includes a first member 94 and a second member 92. First member 94 extends along a first longitudinal axis and defines an inlet aperture 98a at a terminal end thereof. As shown, first member 94 has a rectangular profile. However, first member 94 may be cylindrical or the like.

Second member 92 is connected to first member 94 and extends along a second longitudinal axis which is perpendicular to the first longitudinal axis. Second member 92 includes a first cylindrical portion 95a and a second cylindrical portion 95b. First and second cylindrical portions 95a-b have an equal diameter and are concentric with each other. First and second cylindrical portions 95a-b are offset from each other such that they form a circumferential groove 96 therebetween. An outlet aperture 98b intersects groove 96 transverse to the second longitudinal axis. A passageway or channel 97 extends through first member 94 and second member 92 and is in communication with inlet and outlet apertures 98a-b. In this regard, bone cement injected through inlet aperture 98a passes through passageway 97 and out of outlet aperture 98b.

Figure 7C:
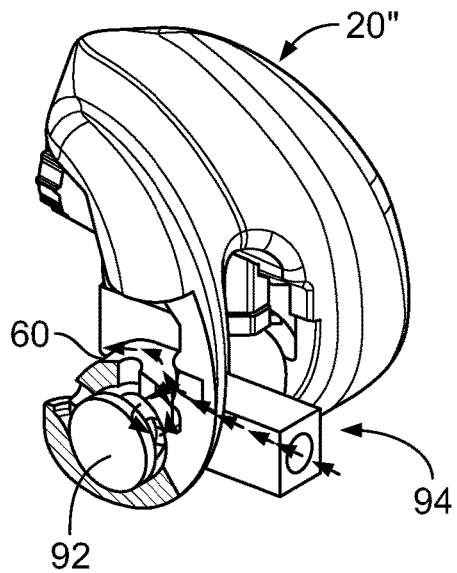
FIG. 7C is a perspective cutaway view of an assembly according to an embodiment of the present disclosure including the assembly of FIG. 6A and cement nozzle of FIG. 7A.

FIG. 7C depicts bone cement applicator 90 coupled to femoral component 20" as it would be in use. As shown, first member 94 extends through intercondylar recess 31 while second member 92 extends transversely thereto and into transverse opening 65 at one of lateral or medial condylar portions 32a-b. In this regard, outlet aperture 98b is positioned within transverse opening 65 so that circumferential groove 96 is aligned within openings 63 of hinge housing component 60 and first and second cylindrical portions 95a-b are flush against concave surfaces 35 and 61 of femoral component 20 and hinge housing component 60, respectively. This allows bone cement to be directed out of outlet aperture 98b, into groove 96, and then out of apertures 63 under pressure so that cement fills grooves 64 and extends about convex outer surface 62 of modular housing 60.

Another device included in the system is an osteotome or cutting tool 110. Osteotome 110 is used to cut a femur when performing a TS-to-hinge conversion so as to make room for modular hinge housing 60, as described below. Osteotome 110 includes a body 111 with a through-opening 116 extending entirely therethrough. A proximal end of osteotome has an impact surface 112 for being impacted by a mallet or the like. A distal end of osteotome has a cutting member 114 that extends from body 111. Cutting member 114 has a semi-cylindrical shape to match that of modular hinge housing 60.

FIGS. 8A to 8F depict a method of converting a joint prosthesis from a first type to a more constrained second type of prosthesis in situ. In the method, TS configured femoral component 20' and the first tibial assembly comprising tibial baseplate component 210 and tibial insert 200 had been previously implanted onto a distal femur and proximal tibia, respectively. However, due to collateral ligament laxity and/or some other defect, a revision procedure to a more constrained hinge knee prosthesis is indicated. As such, a subsequent procedure is performed in which the operator gains access to the previously implanted prosthesis and decouples TS configured femoral component 20" from tibial insert 200. Baseplate component 210 and tibial insert 200 are removed from the proximal tibia. However, femoral component 20 remains connected to the femur so that it can be converted to hinge configured femoral component 20" without disrupting the underlying bone by removing the entirety of femoral component.

Figure 8A:
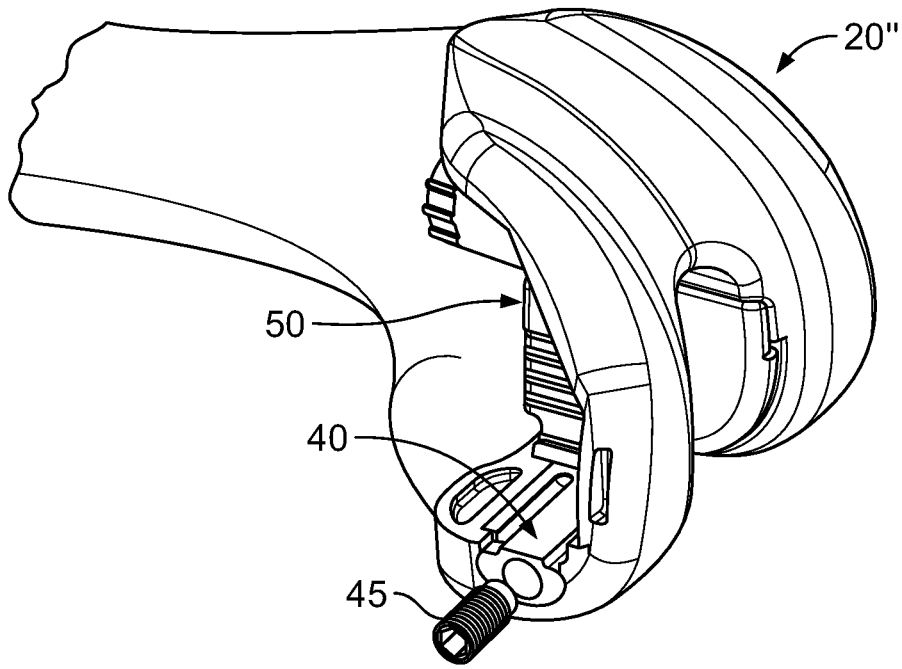
FIGS. 8A-8F depict a method of converting the femoral component of FIG. 2A from a first configuration to a second configuration in situ.

In order to convert TS configured femoral component 20' to hinge configured femoral component 20", the TS modular components are disassembled from femoral component 20. This begins by removal of locking screws 45 from the flanking box locking housings 40, as shown in FIG. 8A. As such, non-threaded posts 46 are also backed out of their positions within apertures 52 of modular box member 50 allowing modular box component 50 to be removed from femoral component 20. In this regard, once locking screws 45 are removed, modular box 50 is slid distally out of intercondylar recess 31. Although modular box 50 may have been cemented to the bone, the direction of longitudinal grooves 53 facilitates an easy removal.

Once modular box 50 is removed from femoral component 20, the femur is resected to make space for modular hinge housing component 60. In this regard, a guide rod 115 is threaded to opening 44 of second box housing 40b, as shown in FIG. 8C. Thereafter, osteotome 110 is advanced over guide rod 115 such that guide rod 115 is received within the through-opening 116 of osteotome 110. Impact surface 112 is then impacted to advance cutting member 114 into the bone thereby resecting the bone to form a curved resected surface configured to contact outer convex surface 62 of modular hinge housing 60. This resection procedure is repeated for the opposite side of the bone.

Once the bone is resected to receive modular hinge housing 60, osteotome 110 and guide rod 115 are removed from the locking box housings 40a-b. Locking box housings 40a-b are then removed from femoral component 20 sequentially. In this regard, medial locking box housing 40b is removed by sliding it in a mediolateral direction toward intercondylar recess 31, as shown in FIG. 8E. Once housing 40b is within intercondylar recess 31 it can be removed through recess 31. This is repeated for the lateral housing 40a. It should be understood that lateral housing 40a could be removed first as it does not matter which housing 40a or 40b is removed first.

At this point the TS configured femoral component 20' has been disassembled down to base femoral component 20. Next, the hinge modular components are assembled to femoral component 20 in order to form hinge configured femoral component 20". This is achieved by first connecting locking wedge 70 to femoral component 20 by inserting it through intercondylar recess 31, as illustrated by one of the arrows in FIG. 8F, so that protrusion 75 is received within walls 29a-c of partial box 27 thereby constraining wedge 70 from mediolateral movement. Locking screw 73 is engaged to a corresponding aperture within partial cam box 27 of femoral component 20. Thereafter, modular axle housing 60 is slid in a mediolateral direction into the previously prepared opening in the bone, as illustrated by the other arrow in FIG. 8F, so that concave surfaces 35b and 61 of femoral component 20 and modular housing 60, respectively, come together to form transverse opening 65. At this point, locking screw 73 is advanced into femoral component 20 causing concave surface 71 of wedge body 76 to come into contact with convex surface 62 of hinge housing 60 and rib 67 to be received within groove 77. Further tightening of screw 73 causes locking wedge 70 to apply a compressive force on hinge housing 60 to secure it in place within femoral component 20.

Thereafter, bone cement is applied between hinge housing 60 and the underlying bone that was just resected. In this regard, bone cement nozzle 90 is introduced into transverse bore 65 of the axle housing, as shown in FIG. 7C. The diameters of the first and second cylindrical portions 95a-b of the nozzle 90 are substantially equal to the diameter of transverse bore 65 of femoral component 20" thereby creating a barrier for the egress of the cement. Pressurization of the cement with the cement gun causes the cement to travel through internal passage 97 of nozzle 90, out through the outlet aperture 98b and through apertures 63 of axle housing 60. Bone cement is thereby delivered and pressurized in the space between axle housing 60 and the adjacent bone. Grooves 64 on axle housing 60 provide interlocking features for the bone cement. Upon delivery of the cement, nozzle 90 is removed, placed on the opposite condyle and the process repeated. Second cylindrical portion 95b of nozzle 90 clears or "squeegees" the cement out of the bore upon removal of thereof thus providing an unobstructed bore 65 for the insertion of axle 100 and corresponding axle bushings 102a-b.

Axle bushings 102a-b are then inserted into transverse opening 65. Second tibial assembly 80 is connected to a proximal end of the tibia such that head 85 of assembly 80 extends proximally therefrom. Head 85 is inserted into intercondylar recess 31 such that the axle opening thereof aligns with transverse opening 65 of hinge configured femoral component 20". Axle 100 is then inserted into transverse opening 65, bushings 102a-b, and the axle opening of head 85 so as to connect second tibial assembly 80 with hinge configured femoral component 20". In this regard, base femoral component 20 was converted from a TS configuration or mode to a more constrained hinge configuration or mode in situ without removing base femoral component 20 from the distal femur. As such, this procedure is performed more quickly than a typical revision procedure and without disrupting the underlying bone.

It should be understood that TS configured femoral component 20' can be preassembled by the manufacturer prior to delivery to the operating room or it can be assembled in the operating room by the surgical team. In this regard, TS configured femoral component is assembled in the reverse order from its disassembly. As such, a first box locking housing 40a is passed through intercondylar recess 31 and slid laterally or medially until partial housing 37 so that convex 42 surface engages concave surface 34a of housing 37. Box locking housing 40 is slid until it abuts interlocking feature 34a. This is repeated for second box locking housing 40b, as can be visualized by FIG. 8E.

Figure 8B:
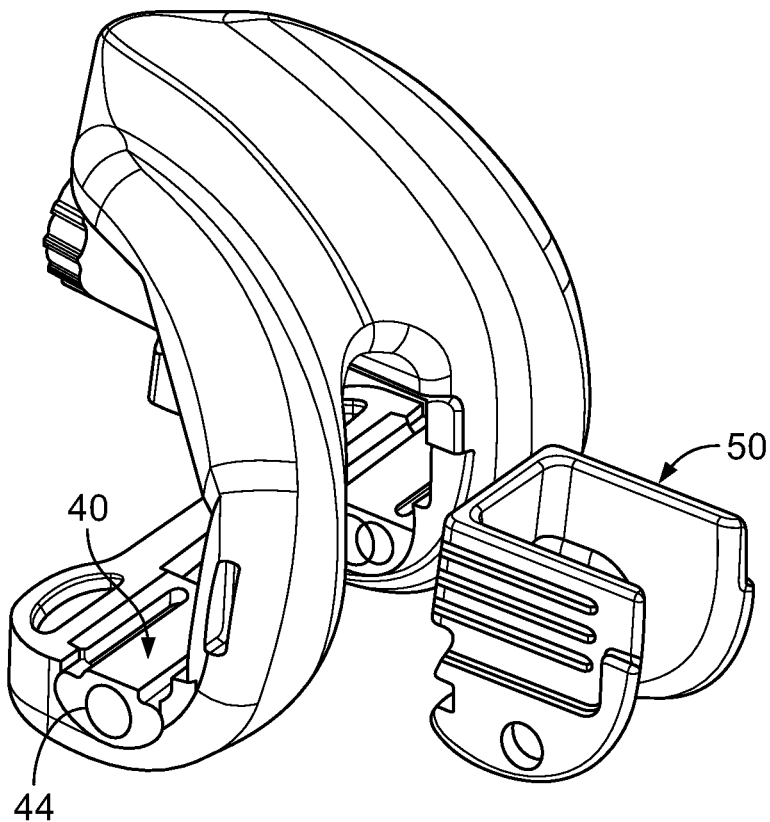
Figure 8C:
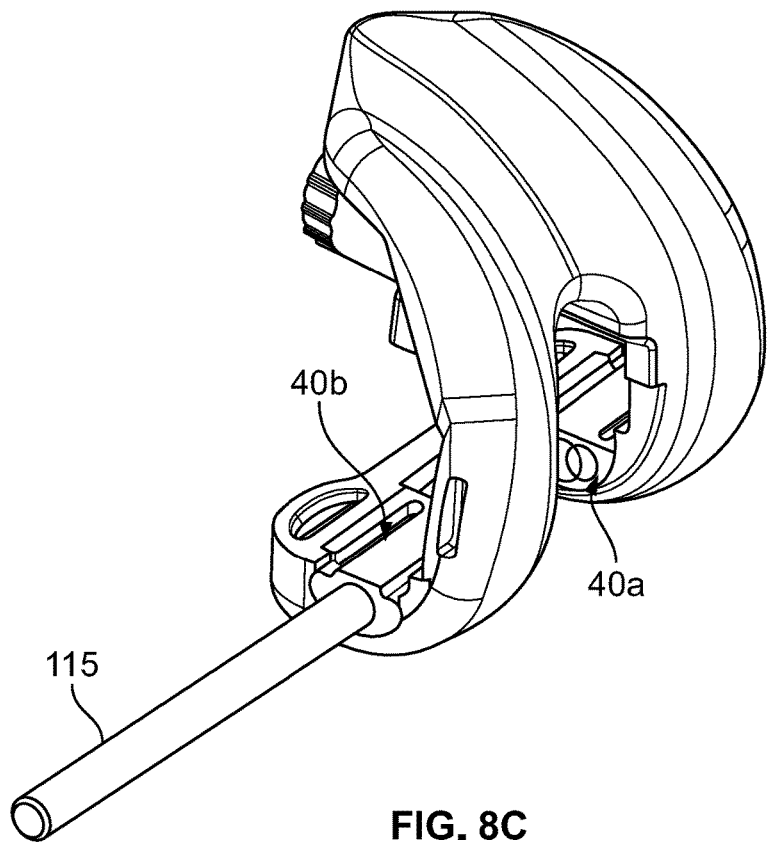
Figure 8D:
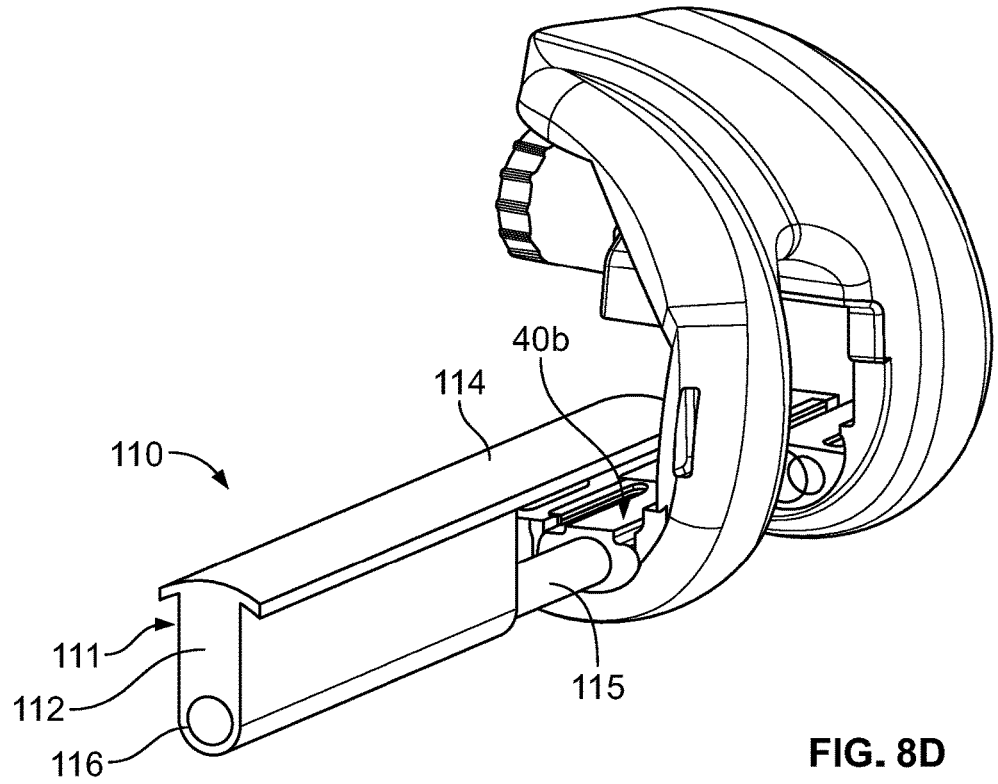
Figure 8E:
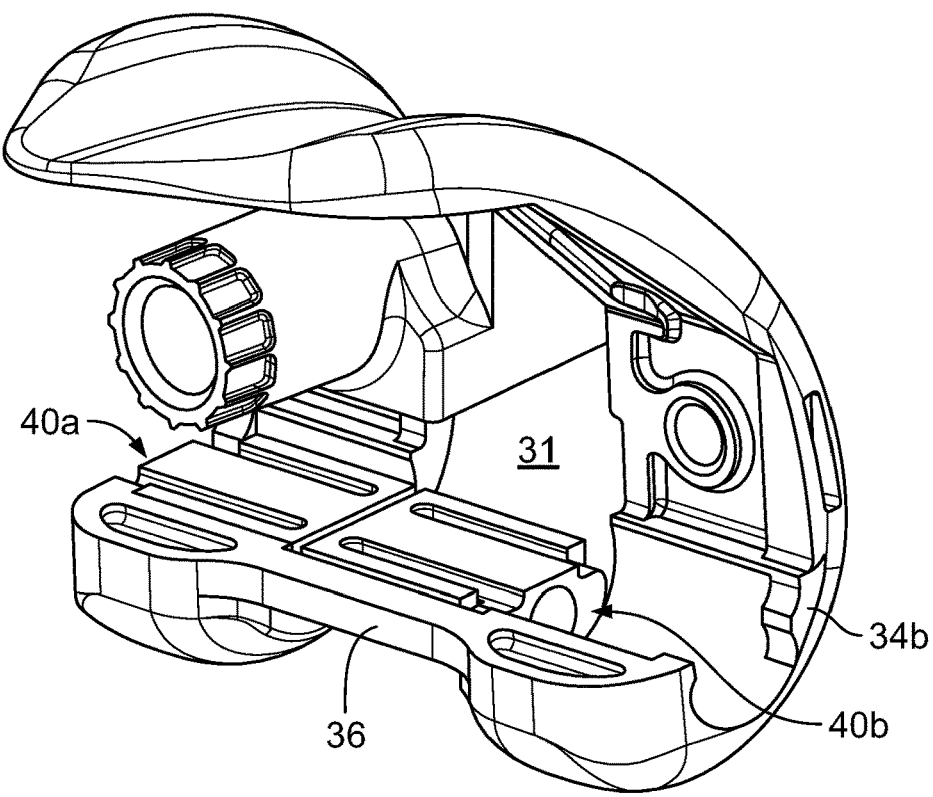
Figure 8F:
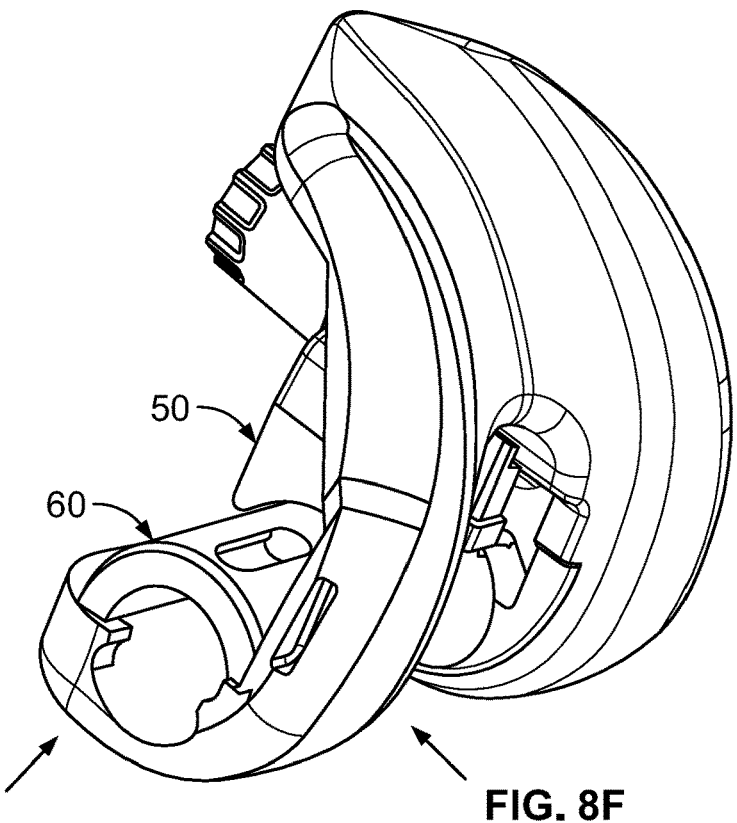

Thereafter, modular cam box 50 is inserted into intercondylar recess 31 between box locking housings 40a-b so that strut 36 is received within slot 51, abutment face abuts 56 partial box walls 29a-b, and apertures 52 align with openings 44 of locking housings 40a-b, as can be visualized by FIG. 8B.

Once modular cam box 50 is in its final seated position, locking screws 45 are threaded into their respective locking housings 50 so that non-threaded posts 46 are received within apertures 52 of modular box 50 to secure it to femoral component 20. Once femoral component 20 is assembled with modular cam box 50 and locking housings 40a-b, TS configured femoral component 20' is ready to be implanted onto a femur, which is resected so as to have a corresponding number of resected surfaces as that of inner surfaces 21-24 of femoral component 20'. TS femoral component 20' is then implanted onto the distal femur and connected with first tibial assembly (200, 210) so that post 202 can articulate with cam surface 59.

Figure 9A:
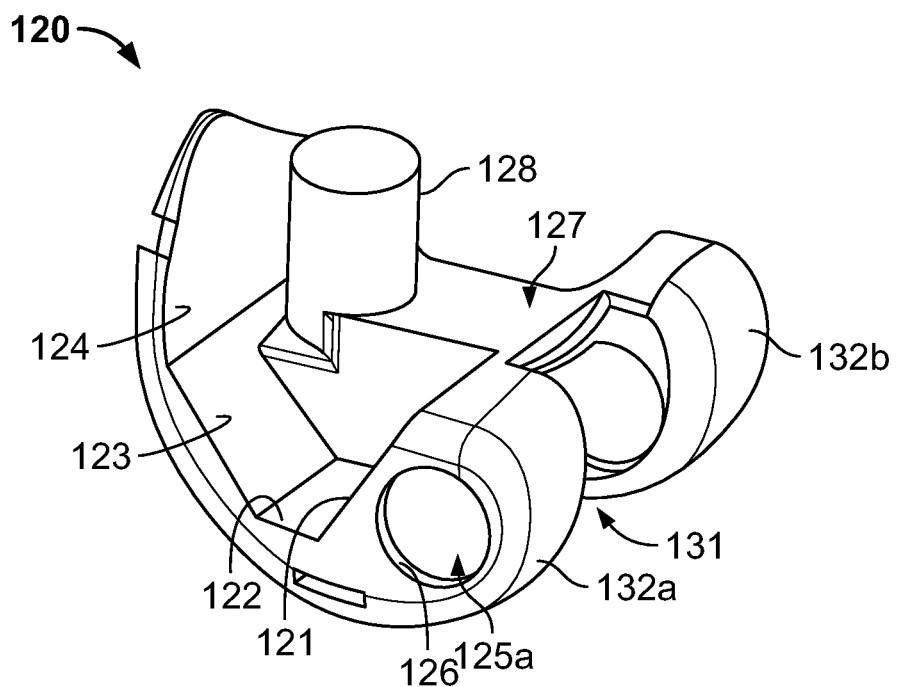
FIG. 9A is a perspective view of a femoral component according to a further embodiment of the present disclosure.

FIG. 9A depicts a femoral component 120 according to another embodiment of the present disclosure. Femoral component 120 is a monolithic body that generally includes a bone facing side, an articular side, and lateral and medial articular portions 132a-b. Lateral and medial condylar portions 132a-b are separated by an intercondylar recess or notch 131. A transverse opening or transverse through-bore 125 extends through a posterior aspect of the lateral and medial condylar portions 132a-b and intersects intercondylar recess 131 such that transverse opening 125 is split by recess into lateral and medial transverse openings 125a-b. In this regard, openings 125a-b are aligned such that they are concentric with each other and form concavely curved surfaces in the shape of a cylinder that extend across lateral and medial condylar portions 132a-b. In addition, transverse opening 125, unlike in femoral component 20, is completely defined by the structure of the monolithic body of femoral component 120, rather than being at least partially defined by modular components that are connected thereto. Femoral component 120 also includes locking ring grooves 126 that are concentric with opening 125 and positioned at the lateral extent of lateral opening 125a and/or medial extent of medial opening 125b.

The bone facing side includes intersecting inner bone facing surfaces 121, 122, 123, and 124. Typically TKA femoral components include five inner bone facing surfaces each corresponding with one of a posterior, anterior, distal, anterior chamfer, and posterior chamfer resected surfaces of a distal femur. While a femoral component may have five of such inner surfaces, femoral component 120 preferably includes four inner bone facing surfaces 121-124 in order to allow for femoral component 120 to have sufficient thickness at a posterior portion thereof for transverse openings 125a-b to extend therethrough. In this regard, a femur is resected to correspond to such inner surfaces 121-124. However, in some embodiments, the bone facing side may have only three bone facing surfaces which would also provide sufficient space to extend opening 125 through the posterior aspect of femoral component. However, four inner bone facing surfaces is preferred because it allows for less bone removal than three inner surfaces while providing for more space for transverse opening 125 than five or more inner surfaces.

The bone facing side also includes a cam box 127 and a stem boss 128. Cam box 127 extends superiorly from femoral component 120. In particular, cam box 127, as shown, interrupts and extends from bone facing surfaces 121-123. However, cam box 127 may extend from any combination of bone facing surfaces 121-124. Cam box 127 is generally more fully formed in the monolithic structure of base femoral component 120 than partial box 27 of femoral component 20 in so far as cam box 127 extends entirely from surface 121 to surface 123 without the use of modular components. However, similar to femoral component 20, cam box 127 utilizes modular components to provide a cam surface that is configured to articulate with a post of a tibial insert, as described further below. Stem boss 128 extends superiorly from cam box 127 and may include an opening therein for receipt of a modular stem (not shown). However, in some embodiments, stem boss 128 may instead be an integral stem incorporated into the structure of femoral component 120. The bone facing side may include a porous material, such as titanium foam and the like for promoting bone ingrowth, such as when femoral component 120 is press-fit to a femur. However, the bone facing side may instead include solid surfaces for instances in which femoral component 120 is cemented to a femur.

As indicated above, femoral component 120 can be used in various TKA configurations. In particular, femoral component 120 can be converted in situ from a TS configuration to a hinge configuration. This allows femoral component 120 to remain affixed to a distal femur in a revision procedure so that instability issues can be addressed by such conversion without the further complication of having to remove femoral component 120 and to resect or otherwise prepare the distal femur for a separate femoral component. Thus, femoral component 120 helps save time in the operating room as well as helps spare bone and potential complications of removing a well affixed prosthesis from underlying bone.

Figure 9B:
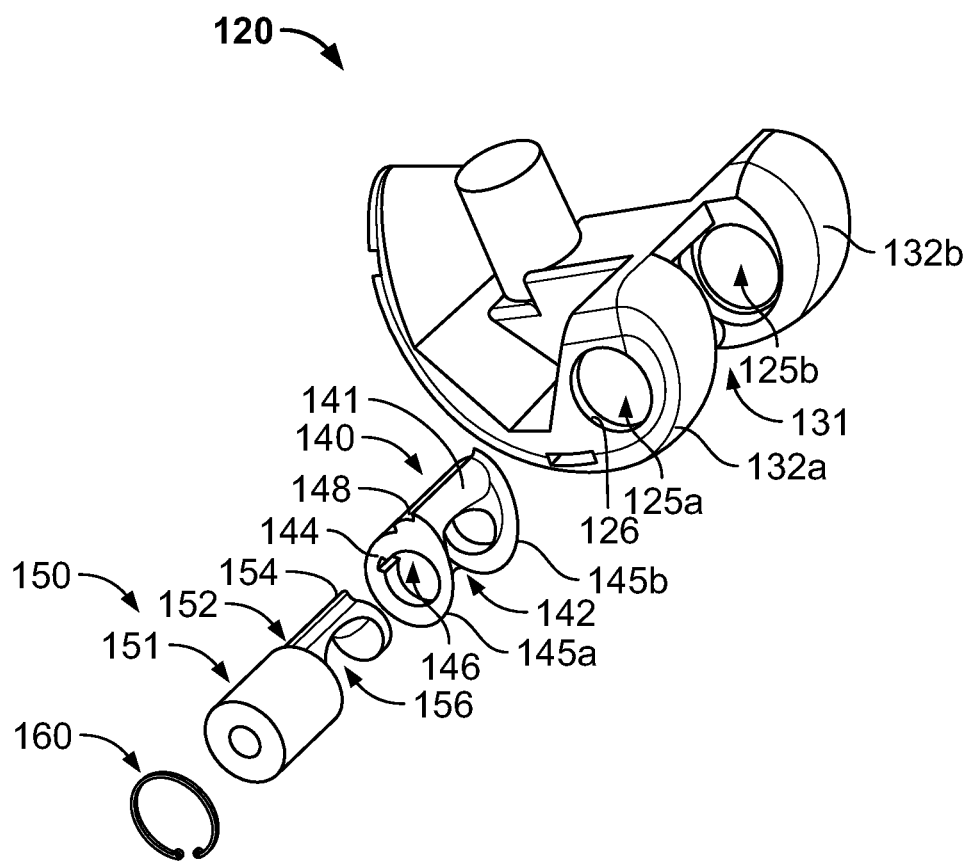
FIG. 9B is an exploded perspective view of an assembly according to a further embodiment of the present disclosure including the femoral component of FIG. 9A.
Figure 9C:
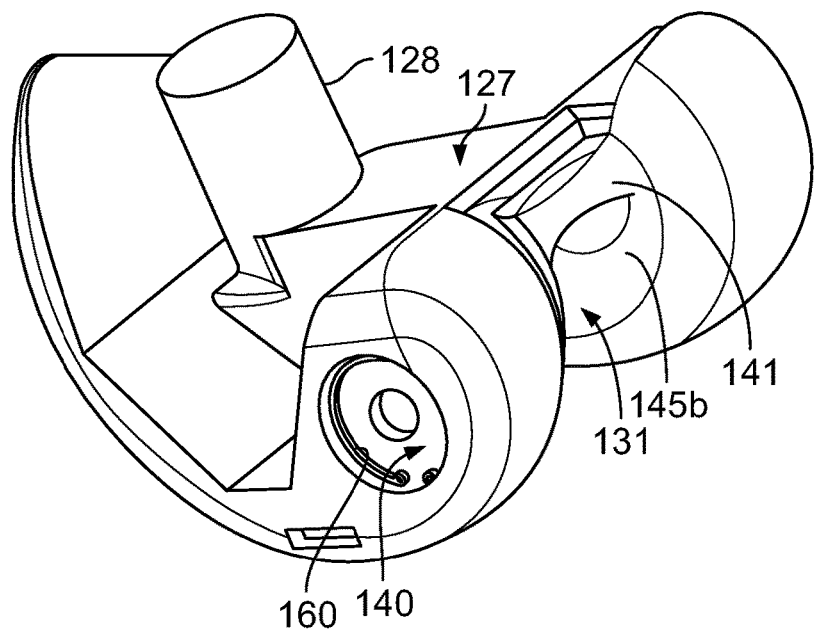
FIG. 9C is a perspective view of the assembly of FIG. 9B, as assembled.

FIGS. 9B and 9C depict femoral component 120 in a TS configuration or TS mode. In this regard, the additional modular components provided in such configuration allow femoral component to be configured for articulation with a post of a tibial insert, such as post 202 of insert 200. Included in this configuration is a cam member or first modular component 140, a cam locking member/axle or second modular component 150, and a locking ring 160.

Cam member 140 is sized and shaped to fit into recess 161 between lateral and medial condylar portions 132a-b and span across recess 131 so as to engage with lateral and medial condylar portions 132a-b. Cam member 140 is intersected by a cam notch or recess 142 which defines a cam portion 141 and opposing lateral and medial tabs or walls 145a-b. Cam member 140 defines a transverse opening 146 that extends laterally-medially through tabs 145a-b and intersects cam recess 142. A longitudinal groove 144 also extends laterally-medially along a superior side of opening 146 such that groove 144 communicates with opening 146. Such groove 144 is configured to slidingly receive a protrusion 154 of cam locking member 150 therein, as described below. Cam member 140 also defined an inferior surface that is a cam surface configured to articulate with a post of a tibial insert, such as post 202, and a superior surface that abuts a corresponding surface in cam box 127 to complete the box. Tabs 145a-b include a keying feature 148 that is shown as teeth or a series of ledges that extend superiorly from one or more of tabs 145a-b. Keying feature 148 allows cam member 140 to engage a corresponding keying feature (not shown) of femoral component 120 so that cam member 140 can engage femoral component 120 in the desired orientation.

Cam locking member 150 has first and second members 151, 152. First member 151 is shown as a hollow cylinder and is dimensioned to be received in either transverse opening 125a or 125b. Second portion 152 extends from first member 151 along a longitudinal axis of cam locking axle 150 and is integral therewith such that first and second members form a monolithic structure. Second portion 152 has a cylindrical profile similar to that of first member 151. However, second portion 152 is machined so that it has a protrusion or rail 154 extending laterally-medially along a length thereof. Such protrusion 154 is configured to be received within groove 144 of cam member 140. Cam axle 150 is also machined to have a recess or notch 156 that corresponds to the recess/notch 142 of cam member 140 so as to effectively become an extension of cam surface 141 of cam member 140 when cam axle 150 is engaged to cam member 140. Thus, when second portion 152 of locking mechanism 150 is positioned within cam member 140, locking mechanism 150 completes cam surface 141 of cam 140 so that such surface 141 is virtually seamless. Cam locking axle 150 is locked into place by locking ring 160 which is configured to be received within locking ring groove 126.

As assembled in the TS configuration, cam member 140 is positioned within recess 131 such that first tab 145a engages lateral condylar portion 132a and second tab 145b engages medial condylar portion 132b. In this regard, cam surface extends across recess, as best shown in FIG. 9C. Moreover, the keying features engage each other such that camming surface 141 is in the appropriate orientation for articulation. In order to lock cam member 140 to femoral component 120, first portion 152 of cam locking axle 150 is positioned within opening 125a within lateral condylar portion 132a of femoral component 120. However, it should be understood that first member 151 can be received within opening 125b in medial condyle. Locking ring 160 is positioned in locking ring groove 126 adjacent to first member 151 but lateral thereto so as to prevent locking axle 150 from moving laterally out of opening 125a. In this position, second portion 152 is positioned within opening 146 of cam member 140 such that protrusion 154 is slideably disposed within recess 144. In this regard, protrusion 154 prevents locking axle 150 and cam member 140 from rotating relative to each other. Moreover, locking axle 150 prevents cam member 140 from moving relative to femoral component 120, thereby securing it in place.

Figure 9D:
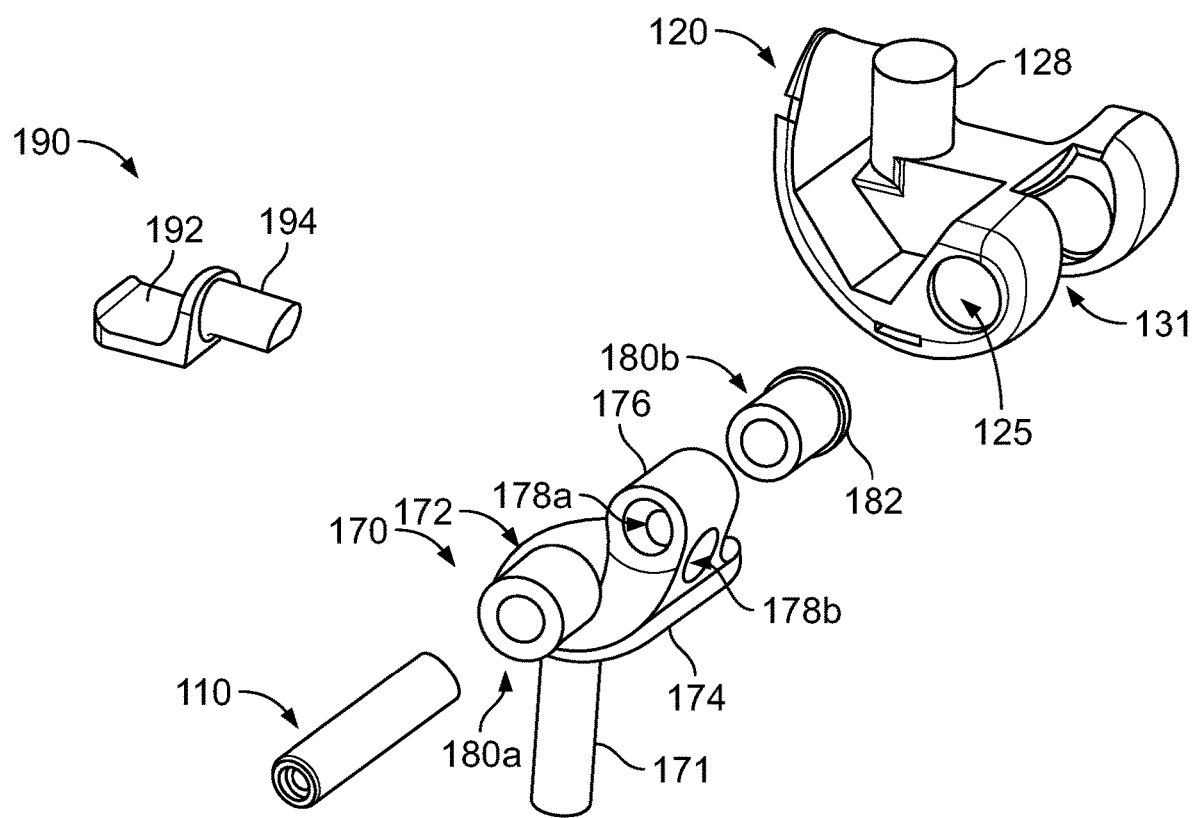
FIG. 9D is an exploded perspective view an assembly according to a yet further embodiment of the present disclosure including the femoral component of FIG. 9A.

Femoral component 120 can be converted from the TS configuration to a hinge configuration in situ. However, it so happens that femoral component 120's default configuration is the hinge configuration. In this regard, femoral component 120 as depicted in FIG. 9A is in the hinge mode and no modular components are needed to convert femoral component 120 to the hinge mode once hinge member 140, locking axle 150, and locking ring 160 are removed. Thus, femoral component 120 as shown in FIG. 9A can be connected straight away to a tibial assembly via an axle. Such tibial assembly is shown is depicted in FIG. 9D and may be identical to that of assembly 80. As such, the tibial assembly includes a bearing component 170, axle 110, axle bushings 180, and a bumper 190, as shown, and also a tibial baseplate component and insert, such as baseplate component 81 and insert 86. Bearing component 170 includes an articular surface 174 for articulation with the tibial insert and a bearing shaft 171 that extends into the tibial baseplate component.

Figure 9E:
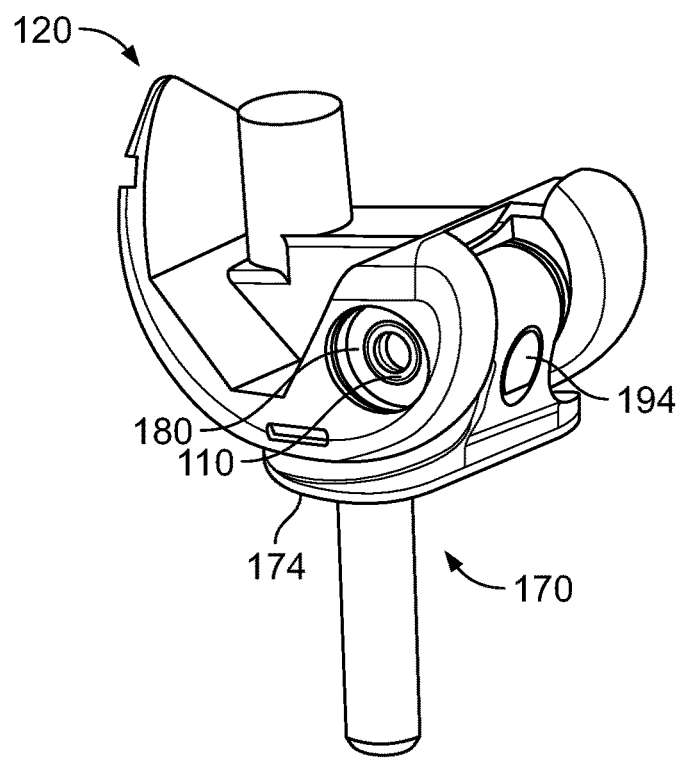
FIG. 9E is a rear perspective view of the assembly of FIG. 9D, as assembled.
Figure 9F:
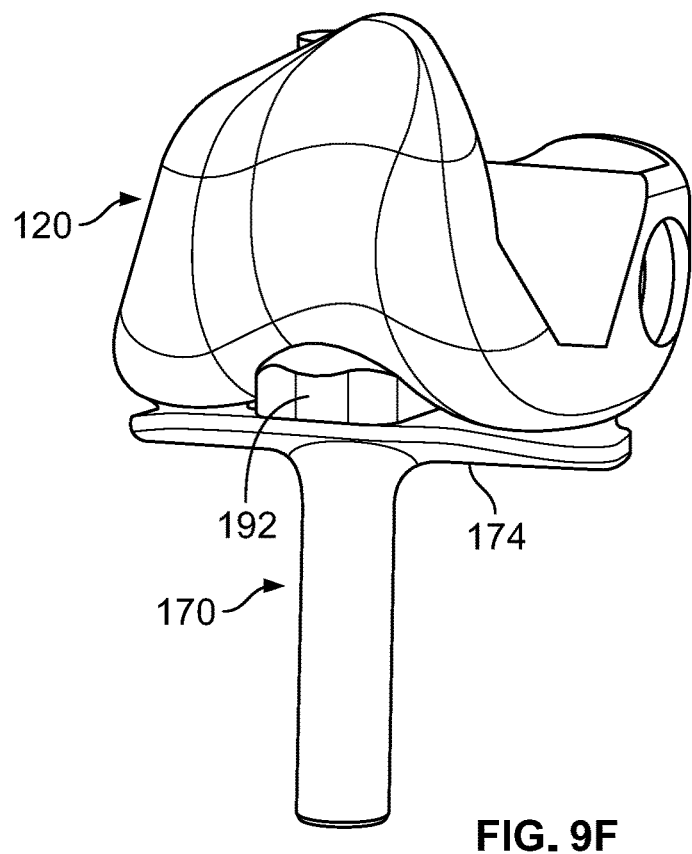
FIG. 9F is a front perspective view of the assembly of FIG. 9D, as assembled.

FIGS. 9E and 9F depict femoral component 120 in the hinge configuration assembled with a corresponding tibial assembly. In this regard, axle 110 is positioned through an axle opening 178a of bearing member 170 and also through transverse openings 125a-b of femoral component 120. Bushings 180a-b are positioned over axle 110 at respective lateral and medial ends thereof and within transverse openings 125a-b. A post 194 of bumper 190 is located within a post opening 178b within head 176 so as to limit hyperextension of femoral component 120 relative to the tibial assembly.

Currently, if a patient has a TS implant which is unstable due to collateral ligament deficiencies, a conversion to a hinged device may be recommended. However, existing TS femoral and tibial implants must be removed in order to perform this conversion. The convertible prosthesis assembly described above allows the surgeon to leave a well fixed, well aligned femoral component 120 in place and still convert femoral component 120 to the hinged configuration.

In this regard, a method of such conversion is now described. In the method, femoral component 120 is preferably preassembled in the TS configuration prior to implantation of the same. In this regard, cam member 140 is inserted into recess 131 of femoral component 120. Cam locking axle 150 is then inserted into opening 125 of femoral component 120 and also opening 146 of cam member 140 such that protrusion 154 is received by groove 144. Thereafter, locking ring 160 is inserted into locking ring groove 126 within opening 125a. However, this assembly can also be done in the operating room. Femoral component 120 in the TS configuration can then be implanted onto a distal end of a femur. As such, the femur may be resected such that it has four resected surfaces to correspond with inner surfaces 121-124 of femoral component 120. After, this initial procedure, which itself may be a revision procedure, the patient may develop instability requiring a revision procedure or a further revision procedure to convert to a hinge prosthesis.

In the revision procedure, the operator gains access to the previously implanted prosthesis via a standard incision. The tibial insert, such as insert 200, is disconnected from femoral component 120. Thereafter, locking ring 160 is removed to allow cam locking axle 150 to slide out of opening 146 of cam member 140 and opening 125a of femoral component 120. This may require an impaction instrument to assist in the removal of locking axle 150. Once cam locking axle 150 is removed, cam member 140 can be removed from recess 131 of femoral component 120. Femoral component 120 remains in place on the distal femur during while such disassembly is performed.

At this point femoral component 120 is in the hinge mode and is, therefore, ready to be assembled with a tibial assembly. In this regard, axle bushings 180a-b are inserted into respective transverse openings 125a-b of femoral component 120 such that flanges 182 are opposite each other and are disposed on the inside of their respective condylar portion 132a-b such that the flanges are at the opposite ends of openings 125a-b relative to locking ring recess 126. Femoral component 120 is then mounted onto bearing component 170 such that head portion 176 extends into recess 131 adjacent flanges 182. Once second opening 178a of bearing component 170 is aligned with axle openings 125a-b, axle 110 is inserted into openings 178a and 125a-b, thereby coupling femoral component 120 to the tibial assembly.

While the foregoing description describes femoral components 20 and 120, which can be converted in situ from a TS configuration to a hinge configuration, it is also contemplated that a tibial assembly connectable thereto can also be converted from a TS configuration to a hinge configuration in situ. For example, baseplate component 81 of FIG. 6D may be utilized in a TS procedure in lieu of baseplate 210 of FIG. 4E. However, insert 200 could be connected to baseplate 81 to operate with femoral component 20 or 120 in their respective TS configurations. Thus, when converted to a hinge configuration, tibial baseplate 81 need not be removed from the patient's tibia. Instead, insert 200 can be disconnected from baseplate 81 and then bearing component 84 or 170 and insert 86 can be coupled to baseplate component 81. Thus, a first tibial assembly may include baseplate component 81 and insert 200, and a second tibial assembly may include baseplate component 81, bearing component 84 or 170, and insert 86.

In addition, while the tibial assemblies described herein include a bearing component 81, 170 that articulates with a respective tibial insert, such as insert 86, it should be understood that the femoral components described herein can be connected to other tibial assemblies that utilize an axle, such as axles 100 and 110. In this regard, it is contemplated that femoral components 20 and 120 can articulate directly with a tibial insert of a hinge prosthesis while also being connected to an axle. As such, a tibial assembly that connects to the femoral components described herein, while in their respective hinge configurations, may not include a bearing component or at least a bearing component that itself has a portion that articulates with a tibial insert.

Furthermore, while the foregoing description describes a system that can convert from a TS configuration to a hinge configuration, it is also contemplated that the system can convert from a PS configuration to a hinge configuration. In this regard, a PS femoral component would be the same as the TS component with the difference being that the PS femoral component would not include a stem boss or intramedullary stem and would instead include pegs that extend superiorly from a bone facing side thereof as is known. While a PS-to-hinge conversion is contemplated, it is more desirable for a TS-to-hinge conversion so that the intramedullary stem can help support the hinge configuration.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A joint prosthesis system for converting a joint prosthesis from a first type to a more constrained second type in situ, comprising:
   a femoral component having an articular side, a bone facing side, and medial and lateral condylar portions, the medial and lateral condylar portions at least partially defining an intercondylar recess located therebetween and a transverse opening extending transverse to the articular side and bone facing side, the intercondylar recess intersecting the transverse opening;
   a first tibial assembly having a tibial baseplate component and a post extending therefrom;
   a first modular component separately formed from the femoral component and being configured to connect thereto, the first modular component having a camming surface configured to articulate with the post of the first tibial assembly;
   a second tibial assembly having a tibial baseplate component and a head extending therefrom, the head defining an axle opening extending therethrough; and
   an axle configured to be received within the axle opening and transverse opening so as to connect the second tibial assembly to the femoral component.

2. The system of claim 1, further comprising a second modular component having a first member and a second member, the first member having a convex surface corresponding to a concave surface of the transverse opening, and the second member extending from the first member and being configured to engage the first modular component so as to secure the first modular component to the femoral component.

3. The system of claim 2, further comprising a third modular component removably connected to the femoral component and having a concave surface at least partially defining the transverse opening.

4. The system of claim 3, further comprising a fourth modular component having a locking body and a threaded fastener connected to the locking body, the locking body being configured to engage the third modular component when the threaded fastener engages the femoral component.

5. The system of claim 1, further comprising a second modular component removably connected to the femoral component and having a concave surface at least partially defining the transverse opening.

6. The system of claim 1, wherein the femoral component includes a strut extending across the intercondylar recess from the lateral condylar portion to the medial condylar portion, and the first modular component includes a plurality of intersecting walls, wherein a first wall of the plurality of walls includes a mating slot configured to receive the strut of the femoral component when the first modular component is connected thereto.

7. The system of claim 1, wherein the femoral component includes a monolithic body, the transverse opening being a cylindrical opening formed within the monolithic body.

8. The system of claim 7, wherein first modular component defines a groove in communication with the opening thereof.

9. The system of claim 7, further comprising a second modular component having a first member configured to be received within the transverse opening and a second member configured to be received within the opening of the first modular component.

10. The system of claim 1, wherein the first modular component includes a pair of opposing walls and an opening extending through at least one of the walls.

11. The system of claim 1, wherein the tibial baseplate of the first tibial assembly is the same as the tibial baseplate of the second tibial assembly.

12. A joint prosthesis system, comprising:
   a femoral component having an articular side, a bone facing side, and medial and lateral condylar portions, the medial and lateral condylar portions at least partially defining an intercondylar recess located therebetween and having a concave surface extending in a mediolateral direction across the medial and lateral condylar portions;
   a first tibial assembly having a tibial baseplate component and a post extending therefrom;
   a first modular component having a camming surface configured to extend at least partially across the intercondylar recess when the first modular component is connected to the femoral component and to articulate with the post of the first tibial assembly; and
   a second modular component having a first member and a second member, the first member having a convex surface corresponding to the concave surface of the femoral component, and the second member extending from the first member and being configured to engage the first modular component so as to secure the first modular component to the femoral component.

13. The system of claim 12, further comprising:
   an axle;
   a second tibial assembly having a tibial baseplate component and a head extending from the tibial baseplate, the head defining an axle opening extending therethrough; and
   a third modular component having a concave surface and being connectable to the femoral component such that, when the third modular component is connected to the femoral component, the concave surfaces of the femoral component and third modular component come together to form a transverse opening extending in the mediolateral direction, the transverse opening being configured to receive the axle therein.

14. The system of claim 12, wherein the second member of the second modular component is a threaded fastener.

15. The system of claim 12, wherein the second member of the second modular component is integral with the first member such that the first and second members form a monolithic body.

16. The system of claim 12, wherein the femoral component includes a monolithic body and the concave surface is a cylindrical surface completely formed by the monolithic body such that the cylindrical surface forms a transverse opening extending through the femoral component.

17. A joint prosthesis system, comprising:
   a femoral component having an articular side, a bone facing side, and medial and lateral condylar portions, the medial and lateral condylar portions at least partially defining an intercondylar recess located therebetween and having a first concave surface extending in a mediolateral direction across the medial and lateral condylar portions;

a first modular component having a second concave surface and being connectable to the femoral component such that, when the first modular component is connected to the femoral component, the first and second concave surfaces come together to form a transverse opening extending in the mediolateral direction;

a first tibial assembly having a tibial baseplate component and a head extending therefrom, the head defining an axle opening extending therethrough; and an axle configured to be received within the transverse opening and axle opening so as to connect the tibial assembly to the femoral component.

18. The system of claim 17, further comprising a second modular component having a locking body and a threaded fastener connected to the locking body, the locking body being configured to engage the first modular component when the threaded fastener engages the femoral component.

19. The system of claim 17, further comprising:

a second tibial assembly having a tibial baseplate component and a post extending therefrom; and a second modular component having a camming surface configured to extend at least partially across the intercondylar recess when the second modular component is connected to the femoral component and to articulate with the post of the second tibial assembly.

\* \* \* \* \*